United States Patent
Yi et al.

(10) Patent No.: US 7,351,843 B2
(45) Date of Patent: Apr. 1, 2008

(54) FURANCARBONYLGUANIDINE DERIVATIVES, THEIR PREPARATION AND PHARMACEUTICAL COMPOSITIONS CONTAINING THEM

(75) Inventors: Kyu Yang Yi, Taejeon-si (KR); Sun Kyung Lee, Taejeon-si (KR); Nak Jeong Kim, Taejeon-si (KR); Jee Hee Suh, Taejeon-si (KR); Soon Hee Hwang, Taejeon-si (KR); Byung Ho Lee, Taejeon-si (KR); Ho Won Seo, Taejeon-si (KR); Sun Kyung Hwang, Taejeon-si (KR); Sung Eun Yoo, Gongju-si (KR); Kyung Hee Lee, Sungnam-si (KR)

(73) Assignees: Korea Research Institute of Chemical Technology (KR); Yuyu, Inc. (KR)

( * ) Notice: Subject to any disclaimer, the term of this patent is extended or adjusted under 35 U.S.C. 154(b) by 140 days.

(21) Appl. No.: 10/581,799

(22) PCT Filed: Dec. 24, 2004

(86) PCT No.: PCT/KR2004/003435

§ 371 (c)(1),
(2), (4) Date: Jun. 3, 2006

(87) PCT Pub. No.: WO2005/063727

PCT Pub. Date: Jul. 14, 2005

(65) Prior Publication Data

US 2007/0299131 A1    Dec. 27, 2007

(30) Foreign Application Priority Data

Dec. 27, 2003    (KR) .......................... 2003-0098027

(51) Int. Cl.
*C07D 307/02*    (2006.01)
*A61K 31/34*    (2006.01)
*A01N 43/08*    (2006.01)

(52) U.S. Cl. .................. 549/484; 549/487; 514/471

(58) Field of Classification Search ................ 549/484, 549/487; 514/471
See application file for complete search history.

(56) References Cited

FOREIGN PATENT DOCUMENTS

WO    WO 99/33460    *    7/1999

OTHER PUBLICATIONS

Wang, Qing-Dong, et al., Pharmacological Possibilities for Protection Against . . . , Cardiovascular Research, vol. 55, pp. 25-37, 2002.
Avkiran, Metin, et al., Na+/H+ Exchange Inhibitors for Cardioprotective . . . , Journal of the American College of Cardiology, vol. 39, No. 5, 2002.
Benos, Dale J., Amiloride: A Molecular Probe of Sodium . . . , The American Physiological Society, vol. 242, C131, 1982.
Scholz, W., et al., How 694, A New Na+/H+ Exchange . . . , Br. J. Pharmacol, vol. 109, pp. 562-568, 1993.
Karmazyn, Morris, Sodium-Hydrogen Exchange in Heart Disease, Science & Medicine, pp. 18-26.

* cited by examiner

*Primary Examiner*—D. Margaret Seaman
*Assistant Examiner*—Nizal S. Chandrakumar
(74) *Attorney, Agent, or Firm*—Lucas & Mercanti, LLP

(57) ABSTRACT

The present invention relates to furancarbonylguanidine derivatives, a preparation method thereof and a pharmaceutical composition comprising the same.

Furancarbonylguanidine derivatives of the present invention inhibit NHE-1 (sodium-hydrogen exchanger isoform 1), which helps recovery of heart function damaged from ischemia/reperfusion and decreases myocardial infarction rate, indicating that they have protective effect on myocardial cells. Thus, furancarbonylguanidine derivatives of the present invention can be effectively used for the prevention and the treatment of ischemic heart diseases such as myocardial infarction, arrhythmia, angina pectoris, etc, and also a promising candidate for a heart protecting agent applied to reperfusion therapy including thrombolytics or cardiac surgery including coronary artery bypass graft, percutaneous transluminal coronary angioplasty, etc.

7 Claims, No Drawings

FURANCARBONYLGUANIDINE DERIVATIVES, THEIR PREPARATION AND PHARMACEUTICAL COMPOSITIONS CONTAINING THEM

This patent application claims the benefit of priority from Korean Patent Application No. 10-2003-0098027 filed Dec. 27, 2003 through PCT Application Serial No. PCT/KR2004/003435 filed Dec. 24, 2004, the contents of which are incorporated herein by reference.

TECHNICAL FIELD

The present invention relates to furancarbonylguanidine derivatives, a preparation method thereof and a pharmaceutical composition comprising the same.

BACKGROUND ART

Ischemic heart diseases including myocardial infarction, arrhythmia and angina pectoris, caused by the myocardial injury and dysfunction that are attributed to ischemia/reperfusion, show high mortality and prevalence rate, and can not be perfectly cured. Thus, intensive scientific and clinical studies on its treatment have been made for the past five decades [Wang, Q D. et al., (2002) Cardiovasc. Res. 55: 25-37].

Ischemia/reperfusion injury is related to various physiological mechanisms such as metabolic changes, immune responses, perturbation of ionic homeostasis, oxygen free radicals, etc. Thus, in order to understand ischemia/reperfusion injury, studies on immune regulators, apoptosis related substances and ion channel regulators, are all relevant [Hearse, D J.(1998) Prog. Cariovasc. Dis. 30: 381-402]. In addition to the studies on mechanisms, new therapeutic approaches and surgical procedures have been actively investigated. However, any novel technique to protect myocardial cells from ischemia/reperfusion has not been adopted clinically, yet. Even after the reperfusion therapy including surgical operations such as coronary artery bypass graft (CABG) and percutaneous transluminal coronary angioplasty (PTCA), and the use of thrombolytics, reperfusion injury such as myocardial infarction, arrhythmia, angina pectoris, decrease of neurocognitive ability, etc, is frequently reported [Robert, M. (2003) Ann. Thorac. Surg. 75: S700-708]. Therefore, it is an urgent need to develop a safe and effective therapy to slow down the progression of myocardial ischemic injury and attenuate the injury by reperfusion.

NHEs (sodium-hydrogen exchangers) are ion transporters expressed in a variety of cells that maintains intracellular pH homeostasis by the electroneutral exchange of intracellular $H^+$ for extracellular $Na^+$. 7 isoforms of NHE have been identified so far, and among them, NHE-1, the major subtype in myocardial cells, has been known to be deeply involved in ischemia/reperfusion injury [Avkiran, M. et. al., (2002) J. Am. Coll. Cardiol. 39: 747-753]. NHE-1 is generally inacive under normal physiological pH ($\approx$7.2). Ischemia brings a rapid fall of intracellular pH (pH$\approx$6.4), more precisely, the production of energy depends on glycolysis under ischemic condition because of the lack of oxygen, resulting in the increase of $H^+$ content in the cell. Then, NHE-1 which has a proton sensor is activated to extrude $H^+$ and to move $Na^+$ into the cell resulting in the increase of intracellular $Na^+$. Ischemia induced the inhibition $Na^+/K^+$ ATPase which is the primary Na+ extrusion pathway from the cardiac myocyte, so that intracellular $Na^+$ is accumulated. Such an increase of intracellular $Na^+$ alters the sarcolemmal $Na^+/Ca^{2+}$ exchanger (NCX) to the reversal mode in a manner that inhibits $Ca^{2+}$ efflux and/or enhances $Ca^{2+}$ influx through this bi-directional mechanism, resulting in a pathologic increase in intracellular $Ca^{2+}$. This intracellular $Ca^{2+}$ overload is assumed to be involved in ischemic and reperfusion injuries by the decomposition of proteins via the activation of protease, phospholipase and endonuclease, the increase of oxygen free radicals via the defect of fat metabolism, and the mutation of DNA, etc. The inhibition of NHE-1 limits the intracellular $Na^+$ and $Ca^{2+}$ overload, which affords the presumable mechanism for cardioprotection against ischemia/reperfusion. The inhibition of NHE-1 does not induce intracellular acidosis because the increased intracellular $H^+$ can be regulated through another ion transpoters. Amiloride, a pyrazin derivative, known as a diuretic, is the first known NHE inhibitor [Benos, D J. (1982) A. J. Physiol. 242: C131]. Amiloride has been confirmed, in experiments using isolated rat hearts, to inhibit NHE-1 and to improve the recovery of cadiac function after ischemia/reperfusion, but showed side effects at the same time such as the additional inhibition on NHE-2 and sodium channel. Thus, it can not used as a cardioprotective agent because of poor selectivity. Studies have been made to discover a NHE-1 selective inhibitor, and NHE-1 selective cariporide (HOE-694), a benzoylguanidine derivative, has been developed by Hoechst Marion Roussel (Aventis) [Scholz, W. et. al., (1993) Br. J. Pharmacol. 109: 562]. Cariporide showed excellent cardiac protective effect in animal models and also showed significant protective effect in a patient undergoing CBGA surgery. Most NHE-1 inhibitors, known so far, have acylguanidine moiety as a pharmacophoric unit such as eniporide, zoniporide, SM-20220, BMS-284640, etc.

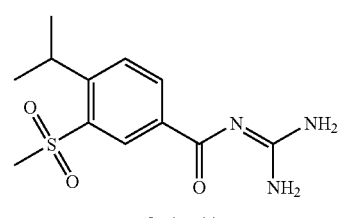

Cariporide

The NHE-1 inhibitor has been proven to improve myocardial contractility and metabolic status, and to reduce arrhythmia, apoptosis, necrosis, and intracellular overload of $Na^+$ and $Ca^{2+}$, indicating that it has a cardioprotective effect against ischemia/reperfusion injury [Karmazyn, M. (2002) Science & Medicine: 18-26]. Thus, NHE-1 selective inhibitor can be effectively used for the prevention and the treatment of ischemic heart diseases such as acute myocardial infarction, arrhythmia, angina pectoris, etc, and also a promising candidate for a heart protecting agent applied to reperfusion therapy or cardiac surgery including coronary artery bypass graft, percutaneous transluminal coronary angioplasty, etc.

DISCLOSURE

Technical Solution

It is an object of the present invention to provide a novel compound to inhibit NHE-1 selectively, to improve myocardial function and to reduce the size of myocardial infarction significantly.

Particularly, it is an object of the present invention to provide a furancarbonylguanidine derivative and pharmaceutically acceptable salts thereof.

It is another object of the present invention to provide a preparation method of the furancarbonylguanidine derivative.

It is a further object of the present invention to provide uses of the furancarbonylguanidine derivative and pharmaceutically acceptable salts thereof.

Best Mode

In order to achieve the above objects, the present invention provides a novel furancarbonylguanidine derivative, pharmaceutically acceptable salts thereof, a preparation method of the same and a pharmaceutical composition containing the same as an effective ingredient.

Hereinafter, the present invention is described in detail.

I. Furancarbonylguanidine Derivatives

The present invention provides a furancarbonylguanidine derivative represented by the following Formula 1 and pharmaceutically acceptable salts thereof.

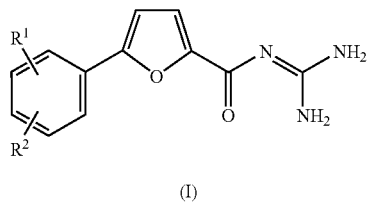

[Formula 1]

(Wherein, $R^1$ and $R^2$ are each independently H, F, Cl, Br, I, $CF_3$, $SO_2CH_3$, $NO_2$, $NH_2$, $C_1$~$C_5$ straight or branched alkyl, or $OR^a$. And, $R^a$ is H, $CF_3$, $C_1$~$C_5$ straight or branched alkyl, or phenyl.)

The present invention also provides, in addition to a furancarbonylguanidine derivative represented by the Formula 1 and pharmaceutically acceptable salts thereof, every possible solvate and hydrate prepared from the same.

Preferably, the compounds of Formula 1 comprise:
1) [5-(2-fluorophenyl)furan-2-ylcarbonyl]guanidine,
2) [5-(3-fluorophenyl)furan-2-ylcarbonyl]guanidine,
3) [5-(4-fluorophenyl)furan-2-ylcarbonyl]guanidine,
4) [5-phenylfuran-2-ylcarbonyl]guanidine,
5) [5-(2-chlorophenyl)furan-2-ylcarbonyl]guanidine,
6) [5-(3-chlorophenyl)furan-2-ylcarbonyl]guanidine,
7) [5-(4-chlorophenyl)furan-2-ylcarbonyl]guanidine,
8) [5-(2-methylphenyl)furan-2-ylcarbonyl]guanidine,
9) [5-(3-methylphenyl)furan-2-ylcarbonyl]guanidine,
10) [5-(4-methylphenyl)furan-2-ylcarbonyl]guanidine,
11) [5-[2-(trifluoromethyl)phenyl]furan-2-ylcarbonyl]guanidine,
12) [5-[3-(trifluoromethyl)phenyl]furan-2-ylcarbonyl]guanidine,
13) [5-[4-(trifluoromethyl)phenyl]furan-2-ylcarbonyl]guanidine,
14) [5-(2-methoxyphenyl)furan-2-ylcarbonyl]guanidine,
15) [5-(3-methoxyphenyl)furan-2-ylcarbonyl]guanidine,
16) [5-(4-methoxyphenyl)furan-2-ylcarbonyl]guanidine,
17) [5-(2-nitrophenyl)furan-2-ylcarbonyl]guanidine,
18) [5-(3-nitrophenyl)furan-2-ylcarbonyl]guanidine,
19) [5-(4-nitrophenyl)furan-2-ylcarbonyl]guanidine,
20) [5-(2-aminophenyl)furan-2-ylcarbonyl]guanidine,
21) [5-(3-aminophenyl)furan-2-ylcarbonyl]guanidine,
22) [5-(4-aminophenyl)furan-2-ylcarbonyl]guanidine,
23) [5-(2-ethylphenyl)furan-2-ylcarbonyl]guanidine,
24) [5-(2-ethoxyphenyl)furan-2-ylcarbonyl]guanidine,
25) [5-(2-isopropoxyphenyl)furan-2-ylcarbonyl]guanidine,
26) [5-(2-phenoxyphenyl)furan-2-ylcarbonyl]guanidine,
27) [5-(2,6-difluorophenyl)furan-2-ylcarbonyl]guanidine,
28) [5-(3,5-difluorophenyl)furan-2-ylcarbonyl]guanidine,
29) [5-(2,4-difluorophenyl)furan-2-ylcarbonyl]guanidine,
30) [5-(2,5-difluorophenyl)furan-2-ylcarbonyl]guanidine,
31) [5-(2,3-difluorophenyl)furan-2-ylcarbonyl]guanidine,
32) [5-(2-chloro-6-fluorophenyl)furan-2-ylcarbonyl]guanidine,
33) [5-(2-fluoro-5-methylphenyl)furan-2-ylcarbonyl]guanidine,
34) [5-(2-methyl-5-fluorophenyl)furan-2-ylcarbonyl]guanidine,
35) [5-(2-methoxy-5-fluorophenyl)furan-2-ylcarbonyl]guanidine,
36) [5-(3,5-dichlorophenyl)furan-2-ylcarbonyl]guanidine,
37) [5-(2,3-dichlorophenyl)furan-2-ylcarbonyl]guanidine,
38) [5-(2,5-dichlorophenyl)furan-2-ylcarbonyl]guanidine,
39) [5-(2-methoxy-5-chlorophenyl)furan-2-ylcarbonyl]guanidine,
40) [5-(2-chloro-5-trifluoromethylphenyl)furan-2-ylcarbonyl]guanidine,
41) [5-(2,6-dimethylphenyl)furan-2-ylcarbonyl]guanidine,
42) [5-(3,5-dimethylphenyl)furan-2-ylcarbonyl]guanidine,
43) [5-(2,5-dimethylphenyl)furan-2-ylcarbonyl]guanidine,
44) [5-(2,3-dimethylphenyl)furan-2-ylcarbonyl]guanidine,
45) [5-(2,6-dimethoxyphenyl)furan-2-ylcarbonyl]guanidine,
46) [5-(2,3-dimethoxyphenyl)furan-2-ylcarbonyl]guanidine,
47) [5-(2,5-dimethoxyphenyl)furan-2-ylcarbonyl]guanidine,
48) [5-(2-methoxy-5-bromophenyl)furan-2-ylcarbonyl]guanidine,
49) [5-(2-hydroxy-5-chlorophenyl)furan-2-ylcarbonyl]guanidine,
50) [5-(2-ethoxy-5-chlorophenyl)furan-2-ylcarbonyl]guanidine, and
51) [5-(2-isopropoxy-5-chlorophenyl)furan-2-ylcarbonyl]guanidine.

The compounds of the above Formula 1 of the present invention are available in the form of pharmaceutically acceptable salts, and acid salts prepared using pharmaceutically acceptable free acids can be useful as pharmaceutically acceptable salts above. Whether it is inorganic or organic, a free acid can be used if it is pharmaceutically acceptable. Examples of the inorganic free acid include hydrochloric acid, bromic acid, sulfuric acid, sulfurous acid and phosphoric acid. Available organic free acids are exemplified by citric acid, acetic acid, malic acid, fumaric acid, gluconic acid, methanesulfonic acid, glycolic acid, succinic acid, tartaric acid, 4-toluenesulfonic acid, galacturonic acid, embonic acid, glutamic acid, and aspartic acid. Preferably, methanesulfonic acid and hydrochloric acid are used.

The acid salts of the compound according to the present invention can be prepared in the conventional method, for example by dissolving the compound of Formula 1 in a water-miscible organic solvent such as acetone, methanol, ethanol or acetonitrile, addition of an excess of aqueous acid, and precipitating the salt with. It is also possible to prepare them by evaporating the solvent or excess of acid in the mixture, followed by drying or filtering off the precipitated salt with suction.

II. Preparation Method

The present invention also provides a preparation method of the furancarbonylguanidine derivative represented by the Formula 1.

Particularly, the present invention provides a preparation method for furancarbonylguanidine compound of Formula 1, as shown in the below Scheme 1, in which carboxylic acid derivative of compound II is reacted with guanidine in the presence of base or with excess of guanidine (preparation method 1).

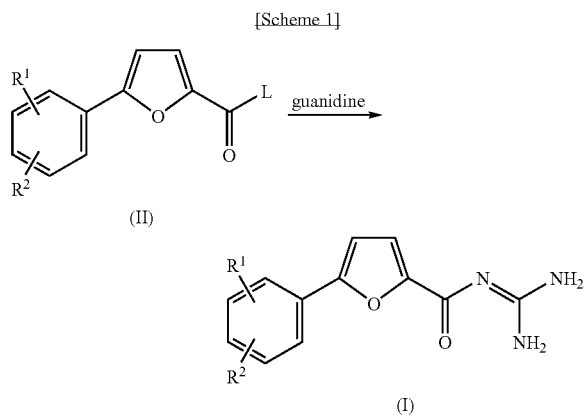

(Wherein, $R^1$ and $R^2$ are as defined in Formula 1, and L is a leaving group that is easily substituted by guanidine.)

Carboxylic acid derivative II is exemplified by ester, acyl halide and acid anhydride derivatives. The ester derivative is alkyl ester (ex, methyl ester or ethyl ester) or active ester derivative (ex, p-nitrophenyl ester, N-hydroxysuccinimide ester, or pentafluorophenyl ester). These carboxylic acid derivatives are prepared with ease from carboxylic acid by the conventional method.

The present invention provides the other preparation method for the compound of Formula 1, which is the other way to prepare furancarbonylguanidine compound by reacting carboxylic acid of compound III with guanidine in the presence of a condensing agent, as shown in the below Scheme 2 (preparation method 2).

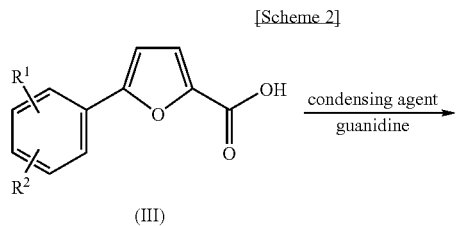

(Wherein, $R^1$ and $R^2$ are as defined in Formula 1.)

The preparation method of a furancarbonylguanidine derivative of Formula 1 of the present invention is described more precisely hereinafter.

(1) Preparation Method 1

In the process of preparing the compound of Formula 1, represented in the Scheme 1, if any of substituents ($R^1$ and $R^2$) of carboxylic acid derivative II is highly sensitive to the reaction, it should be protected by a suitable protecting group. And after the completion of the reaction represented in the Scheme 1, the protecting group has to be removed.

When carboxylic acid derivative II of the Scheme 1 is alkyl ester or active ester, it is preferably reacted with stoicheometric amount or excess of guanidine in a suitable solvent to give compound I.

A reaction solvent can be one of alcohol solvents such as methanol, ethanol and isopropanol, ether solvents such as tetrahydrofuran, dioxane and 1,2-dimethoxyethan, dimethylformamide (DMF) or a mixed solvent of the above. Reaction temperature ranges from room temperature to boiling point of a solvent.

When carboxylic acid derivative II of the Scheme 1 is acyl halide or acid anhydride, it is preferably reacted with excess of guanidine in an appoprate solvent or with stoichiometric amount of guanidine in the presence of base to give compound I. Both inorganic base such as sodium hydroxide, potassium hydroxide, sodium carbonate, etc and organic base such as triethylamine, pyridine, etc, are available.

A reaction solvent can be one of aromatic hydrocarbon solvents such as benzene, toluene, etc, ether solvents such as tetrahydrofuran, halogenized hydrocarbon solvents such as dichloromethane, chloroform, etc, or DMF or a mixed solvent of the above.

(2) Preparation Method 2

In the process of preparing the compound of Formula 1, represented in the Scheme 2, if any of substituents ($R^1$ and $R^2$) of carboxylic acid derivative III is highly sensitive to the reaction, it should be protected by a protecting group. And after the completion of the reaction represented in the Scheme 1, the protecting group has to be removed.

In the Scheme 2, the carboxylic acid compound is reacted with the stoicheometric amount or excess of guanidine in the presence of a condensating agent in a suitable solvent to give compound I. Reaction temperature ranges from room temperature to boiling point of a solvent.

A condensing agent can be selected from a group consisting of N,N-carbonyldiimidazole, dicyclohexylcarbodiimide (DCC), diisopropylcarbodiimide (DIPC), 1-ethyl-3-(3-dimethylaminopropyl)carbodiimide (WSC), diphenylphosphonylazide (DPPA), etc.

A solvent can be selected from a group consisting of ether solvents such as tetrahydrofuran, 1,4-dioxane, etc, aromatic hydrocarbon solvents such as benzene, toluene, etc, halogenized hydrocarbon solvents such as dichloromethane, chloroform, etc, DMF or a mixed solvent of the above.

(3) Preparation of a Starting Material

When carboxylic acid derivative II used in the Scheme 1 is a methyl ester compound (L=OCH$_3$), as shown in the below Scheme 3, it is preferably reacted with phenylboronic acid or stanylphenyl derivative compound IV and 5-halofuran compound V in the presence of a metal catalyst, especially a palladium catalyst, which is Stille-type coupling or Suzuki-type coupling, to give compound II$_1$.

Alternatively Stille or Suzuki reaction can be applied to give compound II$_1$ by using phenyl compound and furan compound represented as compound VI and compound VII in which substituents X and Y are replaced conversely.

[Scheme 3]

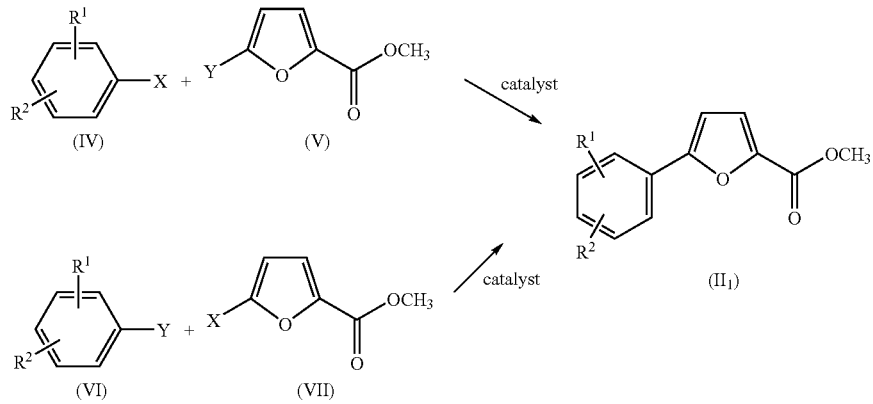

(Wherein, R$^1$ and R$^2$ are as defined in Formula 1, in which X is B(OH)$_2$, BCl$_2$, BBr$_2$, SnBu$_3$, SnMe$_3$, or ZnCl, and Y is halogen (Br, I, Cl) or OSO$_2$CF$_3$.)

In the Scheme 3, phenylboronic acid or stanylphenyl compound IV, or furylboronic acid or stanylfuran compound VII can be purchased or prepared from phenyl halide or 5-halofuran compound by the conventional method.

As a metal catalyst used in the Scheme 3, palladium, nickel or platinum complex is available and palladium catalyst is more preferable among them. As a palladium catalyst, Pd(PPh$_3$)$_4$, Pd—C, PdCl$_2$(PPh$_3$)$_2$, Pd$_2$(dba)$_3$, PdCl$_2$(dppf), [PdCl(allyl)]$_2$, Pd(OAc)$_2$ or PdCl$_2$ is available.

In the Scheme 3, in order to accelerate the reaction and to increase yield, phosphine compound such as PPh$_3$, P-(o-tolyl)$_3$ or PBu$_3$ can be additionally added, and metal salt like lithium chloride, lithium bromide or lithium iodide can also be used as an additive.

In the Scheme 3, 1-3 equivalents of base is used for the Suzuki-type reaction. Applicable bases are exemplified by tertiary amine organic bases such as triethylamine, isopropylethylamine, etc, and inorganic bases such as sodium carbonate, potassium carbonate, potassium hydroxide, sodium hydroxide, cesium carbonate, barium hydroxide, etc. When an inorganic base is difficult to dissolve in an organic solvent, it is used as an aqueous solution, for which the preferable concentration of the inorganic base is 0.5-4 M.

In the Scheme 3, a reaction solvent can be used one of ether solvents such as tetrahydrofuran, dioxane and 1,2-dimethoxyethane, aromatic hydrocarbon solvents such as benzene, toluene and xylene, alcohol solvents such as methanol and ethanol, DMF, acetonitrille, ethyl acetate or a mixed solvent of the above. Reaction temperature ranges from room temperature to boiling point of a solvent.

Carboxylic acid compound III, a starting material of Scheme 2, can be prepared by hydrolyzing ester compound II$_1$, prepared in the Scheme 3, in the presence of base by the conventional method.

Other compounds except methyl ester compound, used as a starting material II in the Scheme 1, can be prepared by the same method as described in the Scheme 3 or from carboxylic acid compound III by the conventional method.

III. Use

The present invention also provides a pharmaceutical composition for cardioprotection containing furancarbonylguanidine derivatives represented by the above Formula 1 and their pharmaceutically acceptable salts as an effective ingredient.

The derivatives and their salts of the present invention have cardioprotective effect by inhibiting NHE-1 selectively. Particularly, the compounds of the present invention showed potent NHE-1 inhibitory effect in human NHE-1 expressing cells and also showed cardioprotective effect in Langendorff's ischemic heart model using isolated rat heart, dose-dependently, by improvement on recovery of cardiac function (left ventricular developed pressure, LVDP) from injury caused by reperfusion. The compounds of the present invention also showed strong anti-ischemic activity in ischemic myocardial models using anesthetized white rats by decreasing the size of myocardial infarction dose-dependently. As explained above, the compounds of the present invention have excellent NHE-1 inhibitory effect and cardioprotective effect after ischemia/reperfusion, in vivo and in vitro as well. Therefore, the compounds of the present invention can be effectively used for the prevention and the treatment of ischemic heart diseases such as myocardial infarction, arrhythmia, angina pectoris, etc, and also a promising candidate for a cardioprotective applied to the patients undergoing cardiac surgery including coronary artery bypass graft, percutaneous transluminal coronary angioplasty, etc.

The compound of the present invention can be administered orally or parenterally and be prepared in general forms of pharmaceutical formulation. The compound can be prepared for oral or parenteral administration by mixing with generally used fillers, extenders, binders, wetting agents, disintegrating agents, diluents such as surfactants, or excipients. Solid formulations for oral administration are tablets, pills, dusting powders, granules, capsules and trokeys. The solid formulations are prepared by mixing one or more suitable excipients such as starch, calcium carbonate, sucrose or lactose, gelatin, etc. Except for the simple excipients, lubricants, for example magnesium stearate, talc, etc, can be used. Liquid formulations for oral administration are suspensions, solutions, emulsions and syrups, and the above mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, freeze-drying and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol and gelatin.

The effective dosage of the compound can be determined according to age, weight, gender, administration method, health condition and severity of a disease. For example, the effective dose of the compound for an adult patient having the weight of 70 kg might be 0.1-1000 mg/day and 1-500 mg/day more preferably. And the administration times are determined by a doctor or a pharmacist to be once a day or a few times a day.

[Mode for Invention]

Practical and presently preferred embodiments of the present invention are illustrative as shown in the following Examples.

However, it will be appreciated that those skilled in the art, on consideration of this disclosure, may make modifications and improvements within the spirit and scope of the present invention.

The molecular structure of compounds of the present invention are confirmed by infrared spectroscopy, nuclear magnetic resonance spectroscopy, mass spectroscopy, liquid chromatography, X-ray crystallography, polarimetry, and the comparison between theoretical value of elementary analysis of a representative compound and experimental value of it.

Preparative Example 1

Preparation of furan-2-carboxylic acid methyl ester derivative

<1-1> 5-(2-fluorophenyl)furan-2-carboxylic acid methyl ester

Methyl 5-bromo-2-furoate (300 mg, 1.46 mmol) was dissolved in toluene (6 ml), to which 2-fluorophenylboronic acid (246 mg, 1.76 mmol) dissolved in methanol (0.5 ml) was added. And 2 M $Na_2CO_3$ solution (0.8 ml, 1.76 mmol) was added thereto. Catalytic amount of $Pd(PPh_3)_4$ (51 mg) was also added thereto, followed by stirring at 80° C. for 6 hours.

After completion of the reaction, the solution was diluted with water (20 ml) and extracted with ethyl acetate (20 ml×2). The organic layer was washed with brine, dried over anhydrous magnesium sulfate ($MgSO_4$), and concentrated in vacuo. The residue was purified by silica gel column chromatography (hexane:ethyl acetate=6:1), to give 290 mg of a title compound (yield: 90%).

$^1$H NMR(300 MHz, $CDCl_3$) δ 3.94(s, 3H), 6.93(t, 1H), 7.14-7.34(m, 4H), 7.99(m, 1H)

<1-2> 5-(3-fluorophenyl)furan-2-carboxylic acid methyl ester $^1$H NMR(300 MHz, $CDCl_3$) δ 3.85(s, 3H), 6.69(d, 1H), 6.97(m, 1H), 7.18(d, 1H), 7.31(m, 1H), 7.39(dd, 1H), 7.48 (d, 1H)

<1-3> 5-(4-fluorophenyl)furan-2-carboxylic acid methyl ester $^1$H NMR(300 MHz, $CDCl_3$) δ 3.92(s, 3H), 6.68(d, 1H), 7.12(dd, 2H), 7.24(d, 1H), 7.76(dd, 2H)

<1-4> 5-phenylfuran-2-carboxylic acid methyl ester $^1$H NMR(300 MHz, $CDCl_3$) δ 3.91(s, 3H), 6.74(d, 1H), 7.25(d, 1H), 7.35-7.46(m, 3H), 7.81(m, 2H)

<1-5> 5-(2-chlorophenyl)furan-2-carboxylic acid methyl ester $^1$H NMR(300 MHz, $CDCl_3$) δ 3.39(s, 3H), 7.21(d, 1H), 7.28(m, 2H), 7.34(dd, 1H), 7.46(dd, 1H), 7.99(dd, 1H)

<1-6> 5-(3-chlorophenyl)furan-2-carboxylic acid methyl ester $^1$H NMR(300 MHz, $CDCl_3$) δ 3.92(s, 3H), 6.75(d, 1H), 7.24(d, 1H), 7.33(d, 2H), 7.65(d, 1H), 7.76 (d, 1H)

<1-7> 5-(2-methylphenyl)furan-2-carboxylic acid methyl ester $^1$H NMR(200 MHz, $CDCl_3$) δ 2.52(s, 3H), 3.91(s, 3H), 6.63(d, 1H), 7.25-7.29(m, 4H), 7.77-7.73(m, 1H)

<1-8> 5-(3-methylphenyl)furan-2-carboxylic acid methyl ester $^1$H NMR(300 MHz, $CDCl_3$) δ 2.42(s, 3H), 3.94(s, 3H), 6.74(d, 1H), 7.18(d, 1H), 7.26(d, 1H), 7.33(dd, 1H), 7.60(d, 1H), 7.64(s, 1H)

<1-9> 5-(4-methylphenyl)furan-2-carboxylic acid methyl ester $^1$H NMR(300 MHz, $CDCl_3$) δ 2.31(s, 3H), 3.84(s, 3H), 6.61(d, 1H), 7.15(d, 2H), 7.17(d, 1H), 7.60(d, 2H)

<1-10> 5-[2-(trifluoromethyl)phenyl]furan-2-carboxylic acid methyl ester $^1$H NMR(300 MHz, $CDCl_3$) δ 3.92(s, 3H), 6.79(d, 1H), 7.26(d, 1H), 7.50(t, 1H), 7.62(t, 1H), 7.80(dd, 2H)

<1-11> 5-[4-(trifluoromethyl)phenyl]furan-2-carboxylic acid methyl ester $^1$H NMR(300 MHz, $CDCl_3$) δ 3.93(s, 3H), 6.85(d, 1H), 7.27(d, 2H), 7.67(d, 2H), 7.89(d, 2H)

<1-12> 5-(2-methoxyphenyl)furan-2-carboxylic acid methyl ester $^1$H NMR(300 MHz, $CDCl_3$) δ 3.91(s, 3H), 3.95(s, 3H), 6.97(d, 1H), 7.03(d, 1H), 7.06(d, 1H), 7.26(d, 1H), 7.32(m, 1H), 8.01(dd, 1H)

<1-13> 5-(3-methoxyphenyl)furan-2-carboxylic acid methyl ester $^1$H NMR(300 MHz, $CDCl_3$) δ 3.86(s, 3H), 3.91(s, 3H), 6.73(d, 1H), 6.73-6.92(m, 1H), 7.24(d, 1H), 7.29-7.36(m, 3H)

<1-14> 5-(4-methoxyphenyl)furan-2-carboxylic acid methyl ester $^1$H NMR(300 MHz, $CDCl_3$) δ 3.85(s, 3H), 3.91(s, 3H), 6.61(d, 1H), 6.94(d, 1H), 7.24(d, 1H), 7.71(d, 2H)

<1-15> 5-(3-nitrophenyl)furan-2-carboxylic acid methyl ester $^1$H NMR(300 MHz, $CDCl_3$) δ 3.95(s, 3H), 6.91(d, 1H), 7.29(d, 1H), 7.71(dd, 1H), 7.98(dd, 1H), 8.31(dd, 1H), 8.51(d, 1H)

<1-16> 5-(2-ethylphenyl)furan-2-carboxylic acid methyl ester $^1$H NMR(300 MHz, $CDCl_3$) δ 1.25(t, 3H), 2.86(q, 2H), 3.91(s, 3H), 6.60(d, 1H), 7.24-7.36(m, 4H), 7.65(d, 1H)

<1-17> 5-(2-ethoxyphenyl)furan-2-carboxylic acid methyl ester $^1$H NMR(300 MHz, $CDCl_3$) δ 1.53(t, 3H), 3.91(s, 3H), 4.17(q, 2H), 6.95(d, 1H), 7.03(dd, 1H), 7.07(d, 1H), 7.29(m, 2H), 8.02(dd, 1H)

<1-18> 5-(2-isopropoxyphenyl)furan-2-carboxylic acid methyl ester
$^1$H NMR(300 MHz, CDCl$_3$) δ 1.43(d, 6H), 3.91(s, 3H), 4.71(m, 1H), 6.99(m, 2H), 7.08(d, 1H), 7.25(d, 1H), 7.29 (dd, 1H), 8.02(dd, 1H)

<1-19> 5-(2-phenoxyphenyl)furan-2-carboxylic acid methyl ester
$^1$H NMR(300 MHz, CDCl$_3$) δ 3.91(s, 3H), 6.93(d, 1H), 7.00(m, 3H), 7.13(dd, 1H), 7.20-7.38(m, 5H), 8.10(dd, 1H)

<1-20> 5-(2,3-dichlorophenyl)furan-2-carboxylic acid methyl ester
$^1$H NMR(300 MHz, CDCl$_3$) δ 3.93(s, 3H), 7.23-7.33(m, 3H), 7.48(dd, 1H), 7.90(dd, 1H)

<1-21> 5-(3,5-dichlorophenyl)furan-2-carboxylic acid methyl ester
$^1$H NMR(300 MHz, CDCl$_3$) δ 3.93(s, 3H), 6.78(d, 1H), 7.25(d, 1H), 7.33(dd, 1H), 7.65(d, 2H)

<1-22> 5-(3,5-dimethylphenyl)furan-2-carboxylic acid methyl ester
$^1$H NMR(300 MHz, CDCl$_3$) δ 2.36(s, 6H), 3.92(s, 3H), 6.70(d, 1H), 6.99(s, 1H), 7.24(d, 1H), 7.41(s, 2H)

<1-23> 5-(2,5-dimethoxyphenyl)furan-2-carboxylic acid methyl ester
$^1$H NMR(300 MHz, CDCl$_3$) δ 3.85(s, 3H), 3.90(s, 3H), 3.91(s, 3H), 6.87(m, 2H), 7.05(d, 1H), 7.25(s, 1H), 7.54(d, 1H)

<1-24> 5-(2-fluoro-5-methylphenyl)furan-2-carboxylic acid methyl ester
$^1$H NMR(300 MHz, CDCl$_3$) δ 2.38(s, 3H), 3.93(s, 3H), 6.91(t, 1H), 7.02(m, 1H), 7.11(m, 1H), 7.27(d, 1H), 7.78(d, 1H)

<1-25> 5-(2-methyl-5-fluorophenyl)furan-2-carboxylic acid methyl ester
$^1$H NMR(200 MHz, CDCl$_3$) δ 2.48(s, 3H), 3.92(s, 3H), 6.67(m, 2H), 7.20(m, 1H), 7.27(d, 1H), 7.49(dd, 1H)

<1-26> 5-(2-methoxy-5-fluorophenyl)furan-2-carboxylic acid methyl ester
$^1$H NMR(300 MHz, CDCl$_3$) δ 3.92(s, 3H), 3.93(s, 3H), 6.90(dd, 1H), 7.00(m, 1H), 7.07(d, 1H), 7.25(d, 1H), 7.71 (dd, 1H)

<1-27> 5-(2-methoxy-5-chlorophenyl)furan-2-carboxylic acid methyl ester
$^1$H NMR(200 MHz, CDCl$_3$) δ 3.93(s, 3H), 3.94(s, 3H), 6.90(d, 1H), 7.05(d, 1H), 7.26(m, 1H), 7.98(d, 1H)

<1-28> 5-(2,6-difluorophenyl)furan-2-carboxylic acid methyl ester
Methyl 5-bromo-2-furoate (300 mg, 1.46 mmol) and 2,6-difluorophenylboronic acid (277.3 mg, 1.76 mmol) were dissolved in DME (8 ml), to which Ba(OH)$_2$.H$_2$O (416 mg, 2.20 mmol) in H$_2$O (2.7 ml) was added. Catalytic amount of Pd(dppf).CH$_2$Cl$_2$ (56 mg) was also added thereto. The reaction mixture was heated at 80° C. for 12 hours.

After completion of the reaction, the solution was added with water (20 ml) and extracted with ethyl acetate (20 ml×2). The organic layer was washed with brine, dried over anhydrous magnesium sulfate (MgSO$_4$), and concentrated in vacuo. The residue was purified by silica gel column chromatography (hexane:ethyl acetate=20:1), to give 35 mg of a title compound (yield: 10%).
$^1$H NMR(200 MHz, CDCl$_3$) δ 3.93(s, 3H), 6.90(m, 1H), 7.00(m, 2H), 7.26-7.31(m, 2H)

<1-29> 5-(2,3-difluorophenyl)furan-2-carboxylic acid methyl ester
$^1$H NMR(200 MHz, CDCl$_3$) δ 3.93(s, 3H), 6.97(dd, 1H), 7.18(m, 2H), 7.28(d, 1H), 7.75(m, 1H)

<1-30> 5-(2,5-difluorophenyl)furan-2-carboxylic acid methyl ester
$^1$H NMR(200 MHz, CDCl$_3$) δ 3.93(s, 3H), 6.95-7.17(m, 3H), 7.27(d, 1H), 7.68(m, 1H)

<1-31> 5-(3,5-difluorophenyl)furan-2-carboxylic acid methyl ester
$^1$H NMR(300 MHz, CDCl$_3$) δ 3.93(s, 3H), 6.78(d, 1H), 6.81(m, 1H), 7.25(d, 1H), 7.29(m, 2H)

<1-32> 5-(2,5-dichlorophenyl)furan-2-carboxylic acid methyl ester
$^1$H NMR(300 MHz, CDCl$_3$) δ 3.93(s, 3H), 7.21-7.28(m, 2H), 7.26(d, 1H), 7.39(d, 1H), 7.98(d, 1H)

<1-33> 5-(2,6-dimethylphenyl)furan-2-carboxylic acid methyl ester
$^1$H NMR(300 MHz, CDCl$_3$) δ 2.35(s, 3H), 2.37(s, 3H), 3.91(s, 3H), 6.56(d, 1H), 7.18(m, 2H), 7.27(d, 1H), 7.48(dd, 1H)

<1-34> 5-(2,3-dimethylphenyl)furan-2-carboxylic acid methyl ester
$^1$H NMR(300 MHz, CDCl$_3$) δ 2.34(s, 3H), 2.37(s, 3H), 3.91(s, 3H), 6.55(d, 1H), 7.13-7.21(m, 2H), 7.27(d, 1H), 7.48(dd, 1H)

<1-35> 5-(2,5-dimethylphenyl)furan-2-carboxylic acid methyl ester
$^1$H NMR(300 MHz, CDCl$_3$) δ 2.36(s, 3H), 2.47(s, 3H), 3.92(s, 3H), 6.61(d, 1H), 7.08(d, 1H), 7.15(d, 1H), 7.27(d, 1H), 7.59(s, 1H)

<1-36> 5-(2,6-dimethoxyphenyl)furan-2-carboxylic acid methyl ester
$^1$H NMR(300 MHz, CDCl$_3$) δ 3.80(s, 6H), 3.89(s, 3H), 6.60(m, 3H), 7.29(m, 2H)

<1-37> 5-(2,3-dimethoxyphenyl)furan-2-carboxylic acid methyl ester
$^1$H NMR(200 MHz, CDCl$_3$) δ 3.87(s, 3H), 3.90(s, 3H), 3.91(s, 3H), 6.92(dd, 1H), 7.08(d, 1H), 7.13(dd, 1H), 7.27(d, 1H), 7.57(dd, 1H)

<1-38> 5-(2-chloro-6-fluorophenyl)furan-2-carboxylic acid methyl ester
$^1$H NMR(300 MHz, CDCl$_3$) δ 3.93(s, 3H), 6.79(dd, 1H), 7.10(m, 1H), 7.25-7.34(m, 3H)

<1-39> 5-(2-methoxy-5-bromophenyl)furan-2-carboxylic acid methyl ester
$^1$H NMR(300 MHz, CDCl$_3$) δ 3.93(s, 3H), 3.94(s, 3H), 6.85(d, 1H), 7.04(d, 1H), 7.25(d, 1H), 7.39(dd, 1H), 8.11(d, 1H)

<1-40> 5-(2-hydroxy-5-chlorophenyl)furan-2-carboxylic acid methyl ester
5-(2-methoxy-5-chlorophenyl)furan-2-carboxylic acid methyl ester (200 mg, 0.75 mmol) was dissolved in CH$_2$Cl$_2$ (3 ml), to which 1.65 ml of BBr$_3$ (1 M CH$_2$Cl$_2$ solution) (1.65 mmol) was added at 0° C., followed by stirring at room temperature for 3 hours.

After completion of the reaction, the solution was added with 20 ml of NaHCO$_3$ aqueous solution and extracted with ethyl acetate (30 ml×2). The organic layer was washed with brine, dried over anhydrous magnesium sulfate (MgSO$_4$), and concentrated in vacuo. The residue was purified by silica gel column chromatography (hexane:ethyl acetate=20:1), to give 121 mg of a title compound (yield: 64%).

$^1$H NMR (300 MHz, CDCl$_3$) δ 3.93 (s, 3H), 6.91 (m, 2H), 7.03 (br-s, 1H), 7.18 (dd, 1H), 7.29 (d, 1H), 7.68 (d, 1H)

<1-41> 5-(2-ethoxy-5-chlorophenyl)furan-2-carboxylic acid methyl ester 5-(2-hydroxy-5-chlorophenyl)furan-2-carboxylic acid methyl ester (100 mg, 0.4 mmol) was dissolved in DMF (1.5 ml), to which K$_2$CO$_3$ (82 mg, 0.59 mmol) and iodoethane (38 μl, 0.47 mmol) were added, followed by stirring at room temperature for 3 hours.

After completion of the reaction, the solution was diluted with water (20 ml) and extracted with ethyl acetate (20 ml×2). The organic layer was washed with brine, dried over anhydrous magnesium sulfate (MgSO$_4$), and concentrated in vacuo. The residue was purified by silica gel column chromatography (hexane:ethyl acetate =10:1), to give 84 mg of a title compound (yield: 75%).

$^1$H NMR(300 MHz, CDCl$_3$) δ 1.54(t, 3H), 3.93(s, 3H), 4.15(q, 2H), 6.88(d, 1H), 7.09(d, 1H), 7.24(dd, 1H), 7.25(d, 1H), 7.98(d, 1H)

<1-42> 5-(2-isopropoxy-5-chlorophenyl)furan-2-carboxylic acid methyl ester $^1$H NMR(300 MHz, CDCl$_3$) δ 1.41(s, 3H), 1.43(s, 3H), 3.92(s, 3H), 4.67(m, 1H), 6.89(d, 1H), 7.09(d, 1H), 7.22(dd, 1H), 7.25(d, 1H), 7.89(d, 1H)

EXAMPLE 1

Preparation of [5-(2-fluorophenyl)furan-2-ylcarbonyl]guanidine methanesulfonate

Na (4.6 g, 0.2 mol) was slowly added into methanol (100 ml). Guanidine hydrochloride (19.1 g, 0.2 mol) was added thereto, and the mixture was stirred at room temperature for one hour. The precipitated white solid was removed by filtering, resulting in 2 M of free guanidine base methanol solution.

5-(2-fluorophenyl)furan-2-carboxylic acid methyl ester (200 mg, 0.91 mmol) was dissolved in methanol (4 ml), to which 2 M guanidine (2.7 ml, 5.4 mmol) methanol solution was added, and the mixture was heated at reflux for 12 hours. After completion of the reaction, the solution was added with saturated brine (20 ml) and extracted with ethyl acetate (30 ml×3). The organic layer was washed with 10% brine, dried over anhydrous magnesium sulfate (MgSO$_4$), and concentrated in vacuo. The residue was dissolved in acetone (4 ml), to which methanesulfonic acid (0.2 ml) was added and then cooled down to 0° C. to precipitate solid. The precipitated solid was collected by filtration to give 169 mg of a title compound (yield: 54%).

$^1$H NMR(300 MHz, DMSO-d$_6$) δ 2.39(s, 3H), 7.14(d, 1H, J=3 Hz), 7.55-7.39(m, 3H), 7.69(d, 1H, J=3 Hz), 8.13-8.08 (m, 1H), 8.41(s-br, 4H), 11.19(s-br, 1H)

EXAMPLE 2

Preparation of [5-(3-fluorophenyl)furan-2-ylcarbonyl]guanidine 5-(3-fluorophenyl)furan-2-carboxylic acid methyl ester (250 mg, 1.14 mmol) was dissolved in DMF (3 ml), to which 2 M guanidine solution (3.4 ml, 6.8 mmol) prepared in Example 1 was added, followed by stirring at room temperature for 2 hours. After completion of the reaction, the solution was added with saturated brine (20 ml) and extracted with ethyl acetate (30 ml×3). The organic layer was washed with 10% brine, dried over anhydrous magnesium sulfate (MgSO$_4$), and concentrated in vacuo. The residue was purified by silica gel column chromatography (5% methanol/dichloromethane), to give 252 mg of a title compound (yield: 89%).

$^1$H NMR(300 MHz, CD3OD) δ 6.95(d, 1H), 7.07(m, 1H), 7.19(d, 1H), 7.43(m, 1H), 7.67(m, 2H)

EXAMPLE 3

Preparation of [5-(4-fluorophenyl)furan-2-ylcarbonyl]guanidine 5-(4-fluorophenyl)furan-2-carboxylic acid methyl ester (220 mg, 1.0 mmol) was dissolved in methanol (4 ml), to which 2 M guanidine solution (3.0 ml, 6.0 mmol) prepared in Example 1 was added, and the mixture was heated at reflux for 12 hours. After completion of the reaction, the solution was added with saturated brine (20 ml) and extracted with ethyl acetate (30 ml×3). The organic layer was washed with 10% brine, dried over anhydrous magnesium sulfate (MgSO$_4$), and concentrated in vacuo. The residue was purified by silica gel column chromatography (5% methanol/dichloromethane), to give 127 mg of a title compound (yield: 51%).

$^1$H NMR(300 MHz, DMSO) δ 6.99(d, 1H), 7.07(d, 1H), 7.29(dd, 2H), 7.82(dd, 2H)

EXAMPLE 4

Preparation of [5-phenylfuran-2-ylcarbonyl]guanidine methanesulfonate 66 mg (yield: 46%) of a title compound was obtained by using 5-phenylfuran-2-carboxylic acid methyl ester (128 mg, 0.63 mmol) and 2 M guanidine methanol solution (1.89 ml, 3.78 mmol) according to the method used in the Example 1.

$^1$H NMR(200 MHz, D$_2$O) δ 2.81(s, 3H), 6.97(d, 1H, J=3.7 Hz), 7.45(d, 1H, J=3.7 Hz), 7.52-7.46(m, 3H), 7.85-7.80(m, 2H)

EXAMPLE 5

Preparation of [5-(2-chlorophenyl)furan-2-ylcarbonyl]guanidine 176 mg (yield: 94%) of a title compound was obtained by using 5-(2-chlorophenyl)furan-2-carboxylic acid methyl ester (167 mg, 0.71 mmol) and 2 M guanidine methanol solution (2.1 ml, 4.2 mmol) according to the method used in the Example 2.

$^1$H NMR(300 MHz, CD$_3$OD) δ 7.22(m, 2H), 7.32(dd, 1H), 7.42(dd, 1H), 7.50(d, 1H), 8.13(d, 1H)

EXAMPLE 6

Preparation of [5-(3-chlorophenyl)furan-2-ylcarbonyl]guanidine 139 mg (yield: 47%) of a title compound was obtained by using 5-(3-chlorophenyl)furan-2-carboxylic acid methyl ester (265 mg, 1.12 mmol) and 2 M guanidine methanol solution (3.4 ml, 6.8 mmol) according to the method used in the Example 3.

$^1$H NMR(300 MHz, CD$_3$OD) δ 6.89(d, 1H), 7.15(d, 1H), 7.22-7.34(m, 2H), 7.68(d, 1H), 7.83(s, 1H)

EXAMPLE 7

Preparation of [5-(4-chlorophenyl)furan-2-ylcarbonyl]guanidine methanesulfonate 5-(4-chlorophenyl)furan-2-carboxylic acid (208 mg, 0.93 mmol) was dissolved in THF (5 ml), to which 1,1'-carbonyldiimidazole (CDI) (182 mg, 1.12 mmol) was added, and the mixture was stirred at room temperature for 30 minutes. 2 M guanidine solution (2.73 ml, 5.45 mmol) prepared in Example 1 was added thereto, and the mixture was reacted at room temperature for 12 hours. After completion of the reaction, the solution was added with saturated brine (20 ml) and extracted with ethyl acetate (30 ml×3). The organic layer was washed with 10% brine, dried over anhydrous magnesium sulfate (MgSO$_4$), and concentrated in vacuo. The residue was dissolved in acetone (4 ml), to which methanesulfonic acid (0.2 ml) was added and then cooled down to 0° C. to precipitate solid. The precipitated solid was collected by filtration to give 234 mg of a title compound (yield: 70%).

$^1$H NMR(300 MHz, DMSO-d$_6$) δ 6.81(d, 2H), 7.08(d, 1H), 7.33(d, 2H), 7.75(d, 2H)

EXAMPLE 8

Preparation of [5-(2-methylphenyl)furan-2-ylcarbonyl]guanidine methanesulfonate 316 mg (yield: 94%) of a title compound was obtained by using 5-(2-methylphenyl)furan-2-carboxylic acid (200 mg, 1.0 mmol), CDI (193 mg, 1.19 mmol) and 2 M guanidine methanol solution (2.97 ml, 5.94 mmol) according to the method used in the Example 7.

$^1$H NMR(300 MHz, DMSO-d$_6$) δ 2.21(s, 3H), 2.50(s, 3H), 6.57(d, 1H, J=3 Hz), 7.07(d, 1H, J=3 Hz), 7.07(m, 3H), 7.80(m, 1H)

EXAMPLE 9

Preparation of [5-(3-methylphenyl)furan-2-ylcarbonyl]guanidine 96 mg (yield: 39%) of a title compound was obtained by using 5-(3-methylphenyl)furan-2-carboxylic acid methyl ester (215 mg, 1.0 mmol) and 2 M guanidine methanol solution (3 ml, 6.0 mmol) according to the method used in the Example 3.

$^1$H NMR(300 MHz, CD$_3$OD) δ 2.41(s, 3H), 6.86(d, 1H), 7.15(s, 1H), 7.18(d, 1H), 7.31(dd, 1H), 7.73(s, 1H)

EXAMPLE 10

Preparation of [5-(4-methylphenyl)furan-2-ylcarbonyl]guanidine methanesulfonate 52 mg (yield: 14%) of a title compound was obtained by using 5-(4-methylphenyl)furan-2-carboxylic acid methyl ester (233 mg, 1.08 mmol) and 2 M guanidine methanol solution (3.2 ml, 6.4 mmol) according to the method used in the Example 1.

$^1$H NMR(300 MHz, DMSO) δ 2.54(s, 6H), 7.41(d, 1H), 7.52(d, 2H), 7.80(d, 1H), 8.03(d, 2H), 8.53(br-s, 4H)

EXAMPLE 11

Preparation of [5-[2-(trifluoromethyl)phenyl]furan-2-ylcarbonyl]guanidine methanesulfonate 190 mg (yield: 62%) of a title compound was obtained by using 5-(2-trifluoromethylphenyl)furan-2-carboxylic acid (312 mg, 1.22 mmol), CDI (237 mg, 1.46 mmol) and 2 M guanidine methanol solution (3.7 ml, 7.4 mmol) according to the method used in the Example 7.

$^1$H NMR(300 MHz, DMSO-d$_6$) δ 2.36(s, 3H), 7.07(d, 1H, J=3 Hz), 7.69(d, 1H, J=3 Hz), 7.97-7.73(m, 4H), 8.34(s-br, 4H), 11.25(s-br, 1H)

EXAMPLE 12

Preparation of [5-[3-(trifluoromethyl)phenyl]furan-2-ylcarbonyl]guanidine methanesulfonate 212 mg (yield: 69%) of a title compound was obtained by using 5-[3-(trifluoromethyl)phenyl]furan-2-carboxylic acid (200 mg, 0.78 mmol), CDI (152 mg, 0.93 mmol) and 2 M guanidine methanol solution (2.3 ml, 4.6 mmol) according to the method used in the Example 7.

$^1$H NMR(300 MHz, DMSO-d$_6$) δ 2.34(s, 3H), 7.54(d, 1H, J=3 Hz), 7.67(d, 1H, J=3 Hz), 7.84-7.76(m, 2H), 8.28(m, 2H), 8.34(s-br, 4H)

EXAMPLE 13

Preparation of [5-[4-(trifluoromethyl)phenyl]furan-2-ylcarbonyl]guanidine 98 mg (yield: 35%) of a title compound was obtained by using 5-[4-(trifluoromethyl)phenyl]furan-2-carboxylic acid methyl ester (252 mg, 0.93 mmol) and 2 M guanidine methanol solution (2.8 ml, 5.6 mmol) according to the method used in the Example 3.

$^1$H NMR(300 MHz, DMSO) δ 7.22(s, 1H), 7.27(d, 1H), 7.82(d, 2H), 8.03(d, 2H)

EXAMPLE 14

Preparation of [5-(2-methoxyphenyl)furan-2-ylcarbonyl]guanidine methanesulfonate 104 mg (yield: 49%) of a title compound was obtained by using 5-(2-methoxyphenyl)furan-2-carboxylic acid methyl ester (191 mg, 0.82 mmol) and 2 M guanidine methanol solution (2.5 ml, 5.0 mmol) according to the method used in the Example 3.

$^1$H NMR(300 MHz, CD$_3$OD) δ 3.97(s, 3H), 7.03-7.11(m, 3H), 7.23(d, 1H), 7.33(m, 1H), 8.10(dd, 1H)

EXAMPLE 15

Preparation of [5-(3-methoxyphenyl)furan-2-ylcarbonyl]guanidine methanesulfonate 12 mg (yield: 4%) of a title compound was obtained by using 5-(3-methoxyphenyl)furan-2-carboxylic acid methyl ester (200 mg, 0.86 mmol) and 2 M guanidine methanol solution (2.6 ml, 5.2 mmol) according to the method used in the Example 1.

¹H NMR(300 MHz, DMSO-d₆) δ 2.34(s, 3H), 3.85(s, 3H), 7.07(d, 1H, J=9 Hz), 7.36(d, 1H, J=3 Hz), 7.56-7.43(m, 3H), 7.66(d, 1H, J=3 Hz), 8.36(s-br, 4H), 11.07(s-br, 1H)

EXAMPLE 16

Preparation of
[5-(4-methoxyphenyl)furan-2-ylcarbonyl]guanidine methanesulfonate 111 mg (yield: 71%) of a title compound was obtained by using 5-(4-methoxyphenyl)furan-2-carboxylic acid (97 mg, 0.44 mmol), CDI (86 mg, 0.53 mmol) and 2 M guanidine methanol solution (1.3 ml, 2.6 mmol) according to the method used in the Example 7.
¹H NMR(300 MHz, DMSO-d₆) δ 2.20(s, 3H), 3.68(s, 3H), 6.96(d, 2H, J=9 Hz), 7.02(d, 1H, J=3 Hz), 7.54(d, 1H, J=3 Hz), 7.77(d, 2H, J=9 Hz), 8.19(s-br, 4H), 11.51(s-br, 1H)

EXAMPLE 17

Preparation of
[5-(2-nitrophenyl)furan-2-ylcarbonyl]guanidine methanesulfonate 146 mg (yield: 62%) of a title compound was obtained by using 5-(2-nitrophenyl)furan-2-carboxylic acid (200 mg, 0.86 mmol), CDI (167 mg, 1.03 mmol) and 2 M guanidine methanol solution (2.6 ml, 5.2 mmol) according to the method used in the Example 7.
¹H NMR(300 MHz, DMSO-d₆) δ 2.38(s, 3H), 7.13(d, 1H, J=3 Hz), 7.70(d, 1H, J=3 Hz), 7.79(t, 1H, J=9 Hz, 6 Hz), 7.96(t, 1H, J=9 Hz, 6 Hz), 7.99(d, 1H, J=9 Hz), 8.09(d, 1H, J=9 Hz), 8.36(s-br, 4H), 11.84(s-br, 1H),

EXAMPLE 18

Preparation of
[5-(3-nitrophenyl)furan-2-ylcarbonyl]guanidine 49 mg (yield: 45%) of a title compound was obtained by using 5-(3-nitrophenyl)furan-2-carboxylic acid methyl ester (100 mg, 0.4 mmol) and 2 M guanidine methanol solution (1.2 ml, 2.4 mmol) according to the method used in the Example 3.
¹H NMR(300 MHz, DMSO-d₆) δ 7.38(d, 1H, J=3.3 Hz), 7.45(d, 1H, J=3.6 Hz), 7.79(t, 1H), 8.24(t, 2H), 8.55(s, 1H)

EXAMPLE 19

Preparation of
[5-(4-nitrophenyl)furan-2-ylcarbonyl]guanidine 205 mg (yield: 58%) of a title compound was obtained by using 5-(4-nitrophenyl)furan-2-carboxylic acid (300 mg, 1.29 mmol), CDI (250 mg, 1.54 mmol) and 2 M guanidine methanol solution (3.9 ml, 7.8 mmol) according to the method used in the Example 7.
¹H NMR(300 MHz, DMSO) δ 7.02(br-s, 2H), 7.08(d, 1H), 7.65(br-s, 1H), 8.00(d, 2H), 8.31(d, 2H)

EXAMPLE 20

Preparation of
(5-(2-aminophenyl)furan-2-ylcarbonyl]guanidine 235 mg (yield: 94%) of a title compound was obtained by using 5-(2-aminophenyl)furan-2-carboxylic acid methyl ester (223 mg, 1.03 mmol) and 2 M guanidine methanol solution (3.1 ml, 6.2 mmol) according to the method used in the Example 2.
¹H NMR(300 MHz, CD₃OD) δ 6.70-6.75(m, 2H), 6.83 (dd, 1H), 7.09(m, 1H), 7.21(d, 1H), 7.56(dd, 1H)

EXAMPLE 21

Preparation of
[5-(3-aminophenyl)furan-2-ylcarbonyl]guanidine 75 mg (yield: 81%) of a title compound was obtained by using 5-(3-aminophenyl)furan-2-carboxylic acid methyl ester (83 mg, 0.38 mmol) and 2 M guanidine methanol solution (1.15 ml, 2.3 mmol) according to the method used in the Example 2.
¹H NMR(300 MHz, CD₃OD) δ 6.69(m, 1H), 6.78(d, 1H), 7.11-7.22(m, 4H)

EXAMPLE 22

Preparation of
[5-(4-aminophenyl)furan-2-ylcarbonyl]guanidine 150 mg (yield: 84%) of a title compound was obtained by using 5-(4-aminophenyl)furan-2-carboxylic acid methyl ester (159 mg, 0.73 mmol) and 2 M guanidine methanol solution (2.2 ml, 4.4 mmol) according to the method used in the Example 2.
¹H NMR(300 MHz, CD₃OD) δ 6.59(d, 1H), 6.73(dd, 2H), 7.15(d, 1H), 7.60(dd, 2H)

EXAMPLE 23

Preparation of
[5-(2-ethylphenyl)furan-2-ylcarbonyl]guanidine 68 mg (yield: 32%) of a title compound was obtained by using 5-(2-ethylphenyl)furan-2-carboxylic acid methyl ester (188 mg, 0.82 mmol) and 2 M guanidine methanol solution (2.5 ml, 5.0 mmol) according to the method used in the Example 3.
¹H NMR(300 MHz, CD₃OD) δ 1.22(t, 3H), 2.90(q, 2H), 6.68(d, 1H), 7.23(d, 1H), 7.29(m, 3H), 7.73(d, 1H)

EXAMPLE 24

Preparation of
[5-(2-ethoxyphenyl)furan-2-ylcarbonyl]guanidine 93 mg (yield: 40%) of a title compound was obtained by using 5-(2-ethoxyphenyl)furan-2-carboxylic acid methyl ester (207 mg, 0.84 mmol) and 2 M guanidine methanol solution (2.5 ml, 5.0 mmol) according to the method used in the Example 3.
¹H NMR(300 MHz, CD₃OD) δ 1.53(t, 3H), 4.20(q, 2H), 7.01-7.09(m, 3H), 7.21(d, 1H), 7.29(dd, 1H), 8.11(dd, 1H)

EXAMPLE 25

Preparation of [5-(2-isopropoxyphenyl)furan-2-ylcarbonyl]guanidine 231 mg (yield: 95%) of a title compound was obtained by using 5-(2-isopropoxyphenyl)furan-2-carboxylic acid methyl ester (215 mg, 0.83 mmol) and 2 M guanidine methanol solution (2.5 ml, 5.0 mmol) according to the method used in the Example 2.

¹H NMR(300 MHz, CD₃OD) δ 1.42(d, 6H), 4.79(m, 1H), 7.04(dd, 1H), 7.08(m, 2H), 7.20(d, 1H), 7.28(dd, 1H), 8.11(dd, 1H)

EXAMPLE 26

Preparation of [5-(2-phenoxyphenyl)furan-2-ylcarbonyl]guanidine 251 mg (yield: 88%) of a title compound was obtained by using 5-(2-phenoxyphenyl)furan-2-carboxylic acid methyl ester (256 mg, 0.87 mmol) and 2 M guanidine methanol solution (2.6 ml, 5.2 mmol) according to the method used in the Example 2.

¹H NMR(300 MHz, CD₃OD) δ 6.94-7.02(m, 4H), 7.13 (m, 2H), 7.26-7.38(m, 4H), 8.22(dd, 1H)

EXAMPLE 27

Preparation of [5-(2,6-difluorophenyl)furan-2-ylcarbonyl]guanidine 35 mg (yield: 79%) of a title compound was obtained by using 5-(2,6-difluorophenyl)furan-2-carboxylic acid methyl ester (40 mg, 0.17 mmol) and 2 M guanidine methanol solution (0.5 ml, 1.0 mmol) according to the method used in the. Example 2.

¹H NMR(300 MHz, CD₃OD) δ 6.86(d, 1H), 7.09(m, 2H), 7.21(d, 1H), 7.39(m, 1H)

EXAMPLE 28

Preparation of [5-(3,5-difluorophenyl)furan-2-ylcarbonyl]guanidine 243 mg (yield: 89%) of a title compound was obtained by using 5-(3,5-difluorophenyl)furan-2-carboxylic acid methyl ester (245 mg, 1.03 mmol) and 2 M guanidine methanol solution (3.1 ml, 6.2 mmol) according to the method used in the Example 2.

¹H NMR(300 MHz, DMSO) δ 7.04(d, 1H), 7.21(m, 2H), 7.49(d, 2H)

EXAMPLE 29

Preparation of [5-(2,4-difluorophenyl)furan-2-ylcarbonyl]guanidine methanesulfonate 369 mg (yield: 81%) of a title compound was obtained by using 5-(2,4-difluorophenyl)furan-2-carboxylic acid methyl ester (300 mg, 1.26 mmol) and 2 M guanidine methanol solution (3.8 ml, 7.6 mmol) according to the method used in the Example 1.

¹H NMR(300 MHz, DMSO-d₆) δ 2.37(s, 3H), 7.18(t, 1H), 7.34(ddd, 1H), 7.51(ddd, 1H), 7.67(d, 1H), 8.37(br-s, 4H), 11.17(br-s, 1H)

EXAMPLE 30

Preparation of [5-(2,5-difluorophenyl)furan-2-ylcarbonyl]guanidine 190 mg (yield: 85%) of a title compound was obtained by using 5-(2,5-difluorophenyl)furan-2-carboxylic acid methyl ester (200 mg, 0.84 mmol) and 2 M guanidine methanol solution (2.5 ml, 5.0 mmol) according to the method used in the Example 2.

¹H NMR(300 MHz, CD₃OD) δ 6.96(dd, 1H), 7.07(m, 1H), 7.20(m, 2H), 7.88(m, 1H)

EXAMPLE 31

Preparation of [5-(2,3-difluorophenyl)furan-2-ylcarbonyl]guanidine 104 mg (yield: 93%) of a title compound was obtained by using 5-(2,3-difluorophenyl)furan-2-carboxylic acid methyl ester (100 mg, 0.42 mmol) and 2 M guanidine methanol solution (1.3 ml, 2.6 mmol) according to the method used in the Example 2.

¹H NMR(300 MHz, CD₃OD) δ 6.96(dd, 1H), 7.24(m, 3H), 7.89(m, 1H)

EXAMPLE 32

Preparation of [5-(2-chloro-6-fluorophenyl)furan-2-ylcarbonyl]guanidine 41 mg (yield: 77%) of a title compound was obtained by using 5-(2-chloro-6-fluorophenyl)furan-2-carboxylic acid methyl ester (48 mg, 0.19 mmol) and 2 M guanidine methanol solution (0.6 ml, 1.2 mmol) according to the method used in the Example 2.

¹H NMR(300 MHz, CD₃OD) δ 6.75(d, 1H), 7.20(m, 2H), 7.42(m, 2H)

EXAMPLE 33

Preparation of [5-(2-fluoro-5-methylphenyl)furan-2-ylcarbonyl]guanidine 161 mg (yield: 87%) of a title compound was obtained by using 5-(2-fluoro-5-methylphenyl)furan-2-carboxylic acid methyl ester (166 mg, 0.71 mmol) and 2 M guanidine methanol solution (2.1 ml, 4.2 mmol) according to the method used in the Example 2.

¹H NMR(300 MHz, CD₃OD) δ 2.38(s, 3H), 6.87(t, 1H), 7.02-7.14(m, 2H), 7.19(d, 1H), 7.94(dd, 1H)

EXAMPLE 34

Preparation of [5-(2-methyl-5-fluorophenyl)furan-2-ylcarbonyl]guanidine 299 mg (yield: 91%) of a title compound was obtained by using 5-(2-methyl-5-fluorophenyl)furan-2-carboxylic acid methyl ester (296 mg, 1.26 mmol) and 2 M guanidine methanol solution (3.8 ml, 7.6 mmol) according to the method used in the Example 2.

¹H NMR(300 MHz, CD₃OD) δ 2.48(s, 3H), 6.79(d, 1H), 6.98(m, 1H), 7.20(d, 1H), 7.27(m, 1H), 7.68(dd, 1H)

EXAMPLE 35

Preparation of [5-(2-methoxy-5-fluorophenyl)furan-2-ylcarbonyl]guanidine 187 mg (yield: 87%) of a title compound was obtained by using 5-(2-methoxy-5-fluorophenyl)furan-2-carboxylic acid methyl ester (196 mg, 0.78 mmol) and 2 M guanidine methanol solution (2.4 ml, 4.8 mmol) according to the method used in the Example 2.

¹H NMR(300 MHz, CD₃OD) δ 3.94(s, 3H), 7.04(m, 2H), 7.08(d, 1H), 7.17(d, 1H), 7.87(dd, 1H)

EXAMPLE 36

Preparation of [5-(3,5-dichlorophenyl)furan-2-ylcarbonyl]guanidine 200 mg (yield: 75%) of a title compound was obtained by using 5-(3,5-dichlorophenyl)furan-2-carboxylic acid methyl ester (240 mg, 0.89 mmol) and 2 M guanidine methanol solution (2.7 ml, 5.4 mmol) according to the method used in the Example 2.

$^1$H NMR(300 MHz, DMSO) δ 7.05(d, 1H), 7.23(d, 1H), 7.52(d, 1H), 7.80(d, 2H)

EXAMPLE 37

Preparation of [5-(2,3-dichlorophenyl)furan-2-ylcarbonyl]guanidine 120 mg (yield: 84%) of a title compound was obtained by using 5-(2,3-dichlorophenyl)furan-2-carboxylic acid methyl ester (131 mg, 0.48 mmol) and 2 M guanidine methanol solution (1.5 ml, 3.0 mmol) according to the method used in the Example 2.

$^1$H NMR(300 MHz, DMSO) δ 7.21(d, 1H), 7.34(d, 1H), 7.59(dd, 1H), 7.75(dd, 1H), 7.98(dd, 1H)

EXAMPLE 38

Preparation of [5-(2,5-dichlorophenyl)furan-2-ylcarbonyl]guanidine 125 mg (yield: 84%) of a title compound was obtained by using 5-(2,5-dichlorophenyl)furan-2-carboxylic acid methyl ester (135 mg, 0.5 mmol) and 2 M guanidine methanol solution (1.5 ml, 3.0 mmol) according to the method used in the Example 2.

$^1$H NMR(300 MHz, DMSO) δ 7.09(d, 1H), 7.27(d, 1H), 7.43(dd, 1H), 7.60(d, 1H), 7.94(d, 1H)

EXAMPLE 39

Preparation of [5-(2-methoxy-5-chlorophenyl)furan-2-ylcarbonyl]guanidine 184 mg (yield: 92%) of a title compound was obtained by using 5-(2-methoxy-5-chlorophenyl)furan-2-carboxylic acid methyl ester (182 mg, 0.68 mmol) and 2 M guanidine methanol solution (2.1 ml, 4.2 mmol) according to the method used in the Example 2.

$^1$H NMR(300 MHz, CD$_3$OD) δ 3.95(s, 3H), 7.06(m, 2H), 7.16(d, 1H), 7.27(dd, 1H), 8.13(d, 1H)

EXAMPLE 40

Preparation of [5-(2-chloro-5-trifluoromethylphenyl)furan-2-ylcarbonyl]guanidine methanesulfonate 320 mg (yield: 90%) of a title compound was obtained by using 5-(2-chloro-5-trifluoromethylphenyl)furan-2-carboxylic acid (242 mg, 0.83 mmol), CDI (148 mg, 0.91 mmol) and 2 M guanidine methanol solution (2.5 ml, 5.0 mmol) according to the method used in the Example 7.

$^1$H NMR(200 MHz, D$_2$O) δ 2.74(s, 3H), 7.50(d, 1H, J=3.7 Hz), 7.64(d, 1H, J=3.9 Hz), 7.72(d, 1H), 7.74-7.72(m, 2H), 8.38(s, 1H)

EXAMPLE 41

Preparation of [5-(2,6-dimethylphenyl)furan-2-ylcarbonyl]guanidine 181 mg (yield: 88%) of a title compound was obtained by using 5-(2,6-dimethylphenyl)furan-2-carboxylic acid methyl ester (185 mg, 0.8 mmol) and 2 M guanidine methanol solution (2.4 ml, 4.8 mmol) according to the method used in the Example 2.

$^1$H NMR(300 MHz, CD$_3$OD) δ 2.34(s, 3H), 2.37(s, 3H), 6.60(d, 1H), 7.14(m, 2H), 7.19(d, 1H), 7.52(dd, 1H)

EXAMPLE 42

Preparation of [5-(3,5-dimethylphenyl)furan-2-ylcarbonyl]guanidine 197 mg (yield: 92%) of a title compound was obtained by using 5-(3,5-dimethylphenyl)furan-2-carboxylic acid methyl ester (190 mg, 0.83 mmol) and 2 M guanidine methanol solution (2.5 ml, 5.0 mmol) according to the method used in the Example 2.

$^1$H NMR(300 MHz, CD$_3$OD) δ 2.32(s, 6H), 6.80(d, 1H)., 6.96(s, 1H), 7.14(d, 1H), 7.47(s, 2H)

EXAMPLE 43

Preparation of [5-(2,5-dimethylphenyl)furan-2-ylcarbonyl]guanidine 230 mg (yield: 94%) of a title compound was obtained by using 5-(2,5-dimethylphenyl)furan-2-carboxylic acid methyl ester (220 mg, 0.95 mmol) and 2 M guanidine methanol solution (2.9 ml, 5.8 mmol) according to the method used in the Example 2.

$^1$H NMR(300 MHz, CD$_3$OD) δ 2.35(s, 3H), 2.46(s, 3H), 6.68(d, 1H), 7.07(d, 1H), 7.15(d, 1H), 7.19(d, 1H), 7.71(s, 1H)

EXAMPLE 44

Preparation of [5-(2,3-dimethylphenyl)furan-2-ylcarbonyl]guanidine 195 mg (yield: 92%) of a title compound was obtained by using 5-(2,3-dimethylphenyl)furan-2-carboxylic acid methyl ester (191 mg, 0.83 mmol) and 2 M guanidine methanol solution (2.5 ml, 5.0 mmol) according to the method used in the Example 2.

$^1$H NMR(300 MHz, CD$_3$OD) δ 2.34(s, 3H), 2.38(s, 3H), 6.60(d, 1H), 7.11-7.20(m, 3H), 7.52(dd, 1H)

EXAMPLE 45

Preparation of [5-(2,6-dimethoxyphenyl)furan-2-ylcarbonyl]guanidine 51 mg (yield: 53%) of a title compound was obtained by using 5-(2,6-dimethoxyphenyl)furan-2-carboxylic acid methyl ester (90 mg, 0.34 mmol) and 2 M guanidine methanol solution (1.0 ml, 2.0 mmol) according to the method used in the Example 2.

$^1$H NMR(300 MHz, CD$_3$OD) δ 3.77(s, 6H), 6.49(d, 1H), 6.69(d, 2H), 7.19(d, 1H), 7.35(d, 1H)

EXAMPLE 46

Preparation of [5-(2,3-dimethoxyphenyl)furan-2-ylcarbonyl]guanidine 317 mg (yield: 83%) of a title compound was obtained by using 5-(2,3-dimethoxyphenyl)furan-2-carboxylic acid methyl ester (346 mg, 1.32 mmol) and 2 M guanidine methanol solution (4.0 ml, 8.0 mmol) according to the method used in the Example 2.

$^1$H NMR(300 MHz, $CD_3OD$) δ 3.84(s, 3H), 3.88(s, 3H), 7.00(dd, 1H), 7.05(d, 1H), 7.13(dd, 1H), 7.19(d, 1H), 7.66(dd, 1H)

EXAMPLE 47

Preparation of [5-(2,5-dimethoxyphenyl)furan-2-ylcarbonyl]guanidine 143 mg (yield: 76%) of a title compound was obtained by using 5-(2,5-dimethoxyphenyl)furan-2-carboxylic acid methyl ester (172 mg, 0.65 mmol) and 2 M guanidine methanol solution (2.0 ml, 4.0 mmol) according to the method used in the Example 2.

$^1$H NMR(300 MHz, $CD_3OD$) δ 3.84(s, 3H), 3.89(s, 3H), 6.87(dd, 1H), 7.00(d, 1H), 7.04(d, 1H), 7.18(d, 1H), 7.71(d, 1H)

EXAMPLE 48

Preparation of [5-(2-methoxy-5-bromophenyl)furan-2-ylcarbonyl]guanidine 138 mg (yield: 89%) of a title compound was obtained by using 5-(2-methoxy-5-bromophenyl)furan-2-carboxylic acid methyl ester (143 mg, 0.46 mmol) and 2 M guanidine methanol solution (1.4 ml, 2.8 mmol) according to the method used in the Example 2.

$^1$H NMR(300 MHz, $CD_3OD$) δ 3.96(s, 3H), 7.04(m, 2H), 7.16(m, 2H), 7.41(d, 1H), 8.27(s, 1H)

EXAMPLE 49

Preparation of [5-(2-hydroxy-5-chlorophenyl)furan-2-ylcarbonyl]guanidine methanesulfonate 73 mg (yield: 30%) of a title compound was obtained by using 5-(2-hydroxy-5-chlorophenyl)furan-2-carboxylic acid methyl ester (167 mg, 0.66 mmol) and 2 M guanidine methanol solution (2 ml, 4.0 mmol) according to the method used in the Example 1.

$^1$H NMR(300 MHz, $CD_3OD$) δ 2.68(s, 3H), 6.91(d, 1H), 7.20(dd, 1H), 7.27(d, 1H), 7.55(d, 1H), 7.99(d, 1H)

EXAMPLE 50

Preparation of [5-(2-ethoxy-5-chlorophenyl)furan-2-ylcarbonyl]guanidine 74 mg (yield: 93%) of a title compound was obtained by using 5-(2-ethoxy-5-chlorophenyl)furan-2-carboxylic acid methyl ester (72 mg, 0.26 mmol) and 2 M guanidine methanol solution (0.77 ml, 1.54 mmol) according to the method used in the Example 2.

$^1$H NMR(300 MHz, $CD_3OD$) δ 1.54(t, 3H), 4.20(q, 2H), 7.06(d, 1H), 7.12(d, 1H), 7.19(d, 1H), 7.27(dd, 1H), 8.15(d, 1H)

EXAMPLE 51

Preparation of [5-(2-isopropoxy-5-chlorophenyl)furan-2-ylcarbonyl]guanidine 122 mg (yield: 91%) of a title compound was obtained by using 5-(2-isopropoxy-5-chlorophenyl)furan-2-carboxylic acid methyl ester (123 mg, 0.42 mmol) and 2 M guanidine methanol solution (1.26 ml, 2.52 mmol) according to the method used in the Example 2.

$^1$H NMR(300 MHz, $CD_3OD$) δ 1.42(s, 3H), 1.44(s, 3H), 4.78(m, 1H), 7.07(d, 1H), 7.12(d, 1H), 7.19(d, 1H), 7.26(dd, 1H), 8.15(d, 1H)

Following experiments were performed to investigate pharmacological actions of the compounds of Formula 1 of the present invention.

EXPERIMENTAL EXAMPLE 1

NHE-1 Inhibitory Effect

Following experiments were performed to investigate NHE-1 inhibitory effect of test samples in cells.

Particularly, human NHE-1 was expressed in PS120 cells originated from CCL39. The cells were cultured in DMEM (Dulbecco's modified Eagle's medium) medium supplemented with 10% fetal bovine serum, 1% penicillin/streptomycin (100× solution) and 1% L-glutamine (200 mM aqueous solution). PS120/NHE-1 cells which were 80-90% grown on a 100 mm dish were treated with trypsin. Then, the cells were washed once with PBS (phosphate buffer saline) and once again with Na-free buffer (138.2 mM choline chloride, 4.9 mM KCl, 1.5 mM $CaCl_2.2H_2O$, 1.2 mM $MgSO_4.7H_2O$, 1.2 mM $KH_2PO_4$, 15 mM D-glucose, 20 mM HEPES, at pH 7.4). After centrifugation, a precipitate was suspended in Na-free buffer containing 20 mM $NH_4Cl$ and 10 μM BCECF-AM (2',7'-bis(2-carboxyethyl)-5,6-carboxyfluorescein acetoxymethyl ester), which was cultured in a 37° C., $CO_2$ incubator for 30 minutes. In order to eliminate $NH_4Cl$ and to wash out BCECF-AM remaining outside of cells, PS120/NHE-1 cells were centrifuged and washed once with Na-free buffer. Cell concentration of the suspension was adjusted to $2.5 \times 10^4$ cells/10 μl, and the suspension was stored at 4° C. in a dark room. 180 μl of HBS buffer (137 mM NaCl, 4.9 mM KCl, 1.5 mM $CaCl_2.2H_2O$, 1.2 mM $MgSO_4.7H_2O$, 1.2 mM $KH_2PO_4$, 15 mM D-glucose, 20 mM HEPES, at pH7.4) and 10 μl of DMSO or the same amount of a compound in DMSO (0.03-10 μM) were distributed in each well of a 96-well plate and mixed well. 10 μl of acidified PS120/NHE-1 cells were added thereto, followed by stirring. After 4 minutes from the cell addition, fluorescence (Excitation 485/444 nm, Emission 535 nm) was measured with a spectrofluorophotometer (XEMINI-XS; Molecular Device) for 96-well plate. The measured fluorescent values were converted into pH by using high-$K^+$/nigericin technique. The acidified cells by $NH_4Cl$ prepulse were recovered by the action of NHE-1. At that time, the concentration of a compound to inhibit 50% of the recovery from intracellular acidification was determined ($IC_{50}$), in order to measure NHE-1 inhibitory effect. In the meantime, cariporide was used as a control.

Results were shown in Table 1.

TABLE 1

NHE-1 inhibitory effect

| Compound | IC$_{50}$ (μM) |
| --- | --- |
| Cariporide | 1.0 |
| Example 1 | 5.1 |
| Example 2 | 1.9 |
| Example 3 | 17.0 |
| Example 4 | 4.4 |
| Example 5 | 0.4 |
| Example 6 | 0.6 |
| Example 7 | 52.7 |
| Example 8 | 0.5 |
| Example 9 | 2.6 |
| Example 10 | >30 |
| Example 11 | 2.9 |
| Example 12 | 13.8 |
| Example 13 | >30 |
| Example 14 | 1.0 |
| Example 15 | 10.9 |
| Example 16 | >30 |
| Example 17 | 8.1 |
| Example 18 | >30 |
| Example 19 | >30 |
| Example 20 | 13.0 |
| Example 21 | >30 |
| Example 22 | >30 |
| Example 23 | 0.5 |
| Example 24 | 0.9 |
| Example 25 | 1.1 |
| Example 26 | 0.5 |
| Example 27 | >30 |
| Example 28 | 0.6 |
| Example 29 | 21.3 |
| Example 30 | 0.6 |
| Example 31 | 6.1 |
| Example 32 | >30 |
| Example 33 | 0.8 |
| Example 34 | 0.2 |
| Example 35 | 0.2 |
| Example 36 | 0.3 |
| Example 37 | 1.5 |
| Example 38 | 0.09 |
| Example 39 | 0.06 |
| Example 40 | >30 |
| Example 41 | 2.8 |
| Example 42 | 2.3 |
| Example 43 | 0.5 |
| Example 44 | 3.4 |
| Example 45 | >30 |
| Example 46 | >30 |
| Example 47 | 3.4 |
| Example 48 | 0.1 |
| Example 49 | 0.06 |
| Example 50 | 0.06 |
| Example 51 | 0.07 |

As shown in the above Table 1, IC$_{50}$ of the control compound cariporide was 1.0 μM, suggesting its excellent NHE-1 inhibitory activity. IC$_{50}$ values of the compounds of Example 2, 4, 5, 6, 8, 9, 11, 14, 23, 24, 25, 26, 28, 30, 33, 34, 35, 36, 37, 38, 39, 41, 42, 43, 44, 47, 48, 49, 50 and 51 were all below 5 μM, indicating that they have NHE-1 inhibitory activity. In particular, those compounds of Example 5, 6, 8, 14, 23, 24, 26, 28, 30, 33, 34, 35, 36, 38, 39, 43, 48, 49, 50 and 51 showed IC$_{50}$ values under 1 μM, indicating that they have similar or significantly greater NHE-1 inhibitory activity than cariporide. And the compounds of Example 38, 39, 48, 49, 50 and 51 showed 10 times as excellent as cariporide on NHE-1 inhibition, whose IC$_{50}$ values were all under 0.1 μM.

The compounds of the present invention can be effectively used as a cardioprotective agent against ischemia/reperfusion injury owing to their strong NHE-1 inhibitory effect.

EXPERIMENTAL EXAMPLE 2

NHE-3 Inhibitory Effect

In order to investigate the selectivity on NHE-1 of each compound, following experiments were performed to measure NHE-3 inhibitory effect of them.

PS120 cell line expressing NHE-3 was prepared. And NHE-3 inhibiting effect of each compound was investigated by the same method as described in the Experimental Example 1.

TABLE 2

NHE-3 inhibitory effect

| Compound | Inhibition at 30 μM |
| --- | --- |
| Example 1 | 16.8% |
| Example 2 | 0% |
| Example 4 | 0% |
| Example 6 | 0% |
| Example 12 | 19.6% |
| Example 17 | 37.6% |

Although the compounds of the present invention showed strong NHE-1 inhibitory effect, they had very weak potency on NHE-3 even at the high concentration of 30 μM. In particular, the compounds of Example 2, 4 and 6 showed no NHE-3 inhibitory effect at all even at the high concentration of 30 μM, even though they had excellent NHE-1 inhibitory effect (their IC$_{50}$ values were 1.9, 4.4 and 0.6 μM, respectively). The above results indicate that the compounds of the present invention have high selectivity to NHE-1.

EXPERIMENTAL EXAMPLE 3

Cardioprotective Effect on Isolated Ischemic Rat Heart Model

The experiment confirming whether the compounds of Formula 1 had the protective effect (antiischemic effect) on isolated ischemic rat heart was accomplished in the below.

100 mg/kg of sodium pentobarbital was injected into abdominal cavity of white male rats (300~450 g, obtained from the experimental animal team of the Korea Research Institute of Chemical Technology) to anesthetize them. Then, an intravenous injection of 1000 U/kg of heparin was performed before isolating their hearts. Particularly, cannula (PE 240) was inserted in the trachea, and artificial respiration was tried upon the rats by using a rodent ventilator. Under that condition, aortic cannula was inserted into the aorta and the heart was excised under retrograde perfusion. The excised heart was hung on Langendorff apparatus quickly and unnecessary tissues on the heart were removed. Perfusion was induced under static pressure (85 mmHg) with 37° C. modified Krebs-Henseleit bicarbonate buffer (composition <mM/L>: 116 NaCl, 4.7 KCl, 1.1 MgSO$_4$, 1.17 KH$_2$PO$_4$, 24.9 NaHCO$_3$, 2.52 CaCl$_2$, 8.32 Glucose, 2.0 Pyruvate) saturated with 95% O$_2$/5% CO$_2$. A metal cannula, to which a latex balloon filled with an ethanol-distilled water mixture (1:1 vol/vol) was linked, was inserted into left ventricle through pulmonary vein. Then, left ventricular pressure transmitted through the balloon was transduced by using pressure transducer, and amplified by using Plugsys bridge amplifier isovolumetrically. Then, the pressure was recorded in a recorder (Linearcorder mark 8 WR 3500). Thereafter, the heart was stabilized for 15 minutes. Then, left ventricular end diastolic pressure (LVEDP) was given by 5 mmHg and such volume of the balloon was kept all through the experiments.

Baseline left ventricular developing pressure (LVDP), heart rate (HR), and coronary flow (CF) were measured. LVDP was calculated by substracting LVSP (left ventricular peak systolic pressure) from LVEDP (left ventricular end diastolic pressure). Double product RPP (rate-pressure product), another important parameter for indirectly assessing cardiac contratile function in Langendorff heart, whose cardiac output could not be measured ordinarily, was calculated by multiplying HR by LVDP. Throughout the experiment, total coronary blood flow was measured by the use of coronary flow probe (diameter: 1.0 mm) installed in aortic cannula with electromagnetic flowmeter. Temperature of heart was steadily maintained by immersing the heart at 37° C. in physiological saline solution to which 95% $O_2$/5% $CO_2$ was constantly supplied. After stabilization for 15 min, the hearts were pre-treated for 10 min with vehicle (0.04% DMSO) or the compound of the present invention or control material. Thereafter, LVDP, HR (heart rate) and CF (coronary flow) were repeatedly measured. Global ischemia was induced by completely shutting off the perfusate for 30 min. Then, the hearts were reperfused and, 30 min later, the parameters for cardiac functions (LVDP, HR and CF) were repeatedly measured. For a negative control, vehicle was treated only, and cariporide was used as a control.

The compounds of the present invention showed excellent cardioprotective activity to ischemic heart isolated from a white rat. Especially, the compounds of Example 2, 4, 6, 8, 9 and 49 showed better improvement of cardiac function (RPP, LVEDP) than cariporide in a dose depedent manner. The compounds of Example 5, 11, 14, 23, 24, 25, 28, 30, 39 and 42 significantly recovered cardiac contractility as RPP over 40%, comparied to negative control (15.5%). In addition to cardiac contractility, according to LVEDP index, the compounds of the present invention also showed significant cardioprotective activity. In conclusion, the compounds of the present invention improve the recovery of heart function from cardiac dysfunction caused by ischemia/reperfusion injury, indicating that they have excellent protective effect on ischemic heart. Therefore, the compounds of the present invention can be effectively used as a preventive and a treating agent for ischemic cardiovascular diseases.

EXPERIMENTAL EXAMPLE 4

Cardioprotective Effect on In Vivo Ischemic Rat Heart Model

In order to investigate if compounds of Formula 1 of the present invention could protect ischemic heart in vivo, antiischemic effects on white rat hearts were examined as follows.

TABLE 3

| Compound | Conc. (μM) | RPP[1] (%) | LVEDP[2] (mmHg) | Compound | Conc. (μM) | RPP (%) | LVEDP (mmHg) |
|---|---|---|---|---|---|---|---|
| Negative control | | 15.5 | 55.3 | Example 14 | 10 | 45.5 | 38.5 |
| Cariporide | 1 | 39.3 | 36.4 | Example 17 | 10 | 39.7 | 34.0 |
| | 3 | 52.6 | 34.3 | Example 23 | 10 | 45.4 | 42.3 |
| | 10 | 73.5 | 22.4 | Example 24 | 10 | 45.3 | 14.0 |
| Example 1 | 10 | 42.7 | 5.7 | Example 25 | 10 | 43.5 | 25.3 |
| Example 2 | 1 | 44.2 | 39.8 | Example 26 | 10 | 2.7 | 32.0 |
| | 3 | 54.2 | 36.3 | Example 28 | 3 | 41.1 | 37.5 |
| | 10 | 78.3 | 21.8 | | 10 | 63.3 | 18.8 |
| Example 4 | 1 | 33.4 | 59.7 | Example 30 | 10 | 64.2 | 21.7 |
| | 10 | 72.8 | 30.3 | Example 33 | 10 | 17.1 | 51.0 |
| Example 5 | 10 | 43.5 | 30.0 | Example 35 | 10 | 27.4 | 46.3 |
| Example 6 | 1 | 64.4 | 23.0 | Example 36 | 10 | 26.8 | 36.0 |
| | 3 | 66.8 | 27.7 | Example 37 | 10 | 39.9 | 16.3 |
| | 10 | 100.7 | 16.8 | Example 38 | 10 | 21.8 | 38.7 |
| Example 8 | 3 | 50.6 | 32.8 | Example 39 | 10 | 42.3 | 23.0 |
| | 10 | 93.2 | 16.5 | Example 42 | 10 | 50.3 | 12.7 |
| Example 9 | 10 | 75.0 | 22.9 | Example 49 | 1 | 41.1 | 35.8 |
| Example 11 | 10 | 66.1 | 18.7 | | 3 | 57.2 | 36.6 |
| | | | | | 10 | 80.5 | 20.7 |

[1]rate pressure product (HR × LVDP)
[2]left ventricular end diastolic pressure

As shown in the Table 3, in negative control, reperfusion RPP (Double Product parameter, LVDP×HR), an index for contractility function, was decreased to 15.5% of pre-treatment RPP, and LVEDP, another index for cardioprotective activity, was significantly increased to 55.3 mmHg from 5 mmHg.

In 10 μM of cariporide treated group, reperfusion contractile function (RPP, LVDP×HR) was 73.5% to the basal value before the induction of global ischemia, which was significantly improved compared to the negative control group. LVEDP was 22.4 mmHg, significantly lower than control. In 1 μM and 3 μM of cariporide treated groups, reperfusion contractile function was significantly improved dose-dependently compared to the negative control group.

75 mg/kg of sodium pentobarbital was injected into abdominal cavity of white male rats (350-450 g, Laboratory Animal Division, Korea Research Institute of Chemical Technology) to anesthetize them. After performing tracheotomy, artificial respiration was performed by 10 Ml/kg of stroke volume and 60/ min. of heart rate. Cannula was inserted into each of vena fermoralis and aorta fermoralis, through which medicines were administered and blood pressure was measured. In the meantime, since body temperature in a ischemic myocardial injury model was very important factor, directly influencing a result, the temperature of a rat was always kept at 37° C. by using a probe for measuring body temperature inserted in rectum and homeothermic blanket control unit. Mean arterial blood pressure and heart rate (HR) of the rat were measured all through the experiments. Statham P23XL pressure transducer (Grass Ins., MA, USA) was used for measuring blood pressure and ECG/RATE Coupler (Hugo Sachs Electronic, Germany) was used for measuring HR. In addition, all the changes were recorded successively by graphtec linearcorder chart recorder (Graphtec Linearcorder WR 3310, Hugo Sachs Electronic).

According to the method of Selye H, left coronary aorta was occluded as follows. Left thoracotomy was performed. That is, the chest of a rat was a little opened. The right chest of the anesthetized rat was pressurized by the middle finger of left hand, so that the heart was pushed out. The heart was fixed gently by the thumb and the index finger of the left hand. A stitch was carefully put on a part including left anterior descending coronary artery (LAD) by a suture needle with operating thread (5-0 silk ligature), and the heart was quickly positioned again in thoracic cavity. Then, both ends of operating thread were exposed outside. Both ends of operating thread were passed through PE tube (PE100, 2.5 cm) and left for 20 minutes for stabilization. A vehicle or a medicine was administered through the cannula inserted in femoral vein, which was left for 30 minutes in order for the medicine to work thoroughly. Cariporide was used for a control group.

PE tube threaded on a string was pushed in the heart and the string near the edge of the tube was pulled by hemostatic pincette to stick PE tube vertically to coronary artery, which was pressurized. 45 minutes later, the coronary artery was occluded. Hemostatic pincette was removed and reperfusion went for 90 minutes.

The coronary artery was reoccluded according to the above method and 2 Ml of 1% Evans blue solution was administered by intravenous injection. The white rat was sacrificed by the over-dose of pentobarbital, which was intravenously injected. The heart was taken and right ventricle and both atria were removed. Left ventricle was 5~6 slice cut horizontally from apex, and each slice was weighed. The surface of each slice was inputted in a computer by using Hi-scope, a compact micro vision system, and Image pro plus program, from which both normal blood flow tissue area stained by blue and non-stained area on each slice was measured. The ratio of non-stained area to the gross area of each slice was calculated, by which the weight of each slice was multiplied to calculate AAR (area at risk) of each slice. All the AARs were added up, which was then divided by the total weight of left ventricle, resulting in the percentage of AAR(%) represented in the below Mathematical Formula 1.

$$AAR(\%) = (\text{Sum of AAR of each slice})/(\text{Total weight of left ventricle}) \times 100 \quad \text{[Mathematical Formula 1]}$$

The heart slice was cultivated for 15 minutes in 1% 2,3,5-triphenyltetrazolium chloride(TTC) phosphate buffer (37° C., pH 7.4), then was fixed for 20~24 hours in 10% formalin solution. 2,3,5-triphenyltetrazolium chloride was reduced by dehydrogenase and cofactor 'NADH' in myocardium for being formazan dye. Therefore, normal tissues had brick-red color thereby. On the contrary, infract zone without dehydrogenase or cofactor was not brick red because 2,3,5-triphenyltetrazolium chloride was not reduced.

A normal area and an infarct zone of each slice were determined by investigating the coloring of tissues by 2,3,5-triphenyltetrazolium chloride by taking advantage of the method used for AAR measurement. All the infarct zones of each slice were added up, which was divided by the total weight of AAR or the weight of a whole left ventricle, resulting in IS(%) represented in the below Mathematical Formula 2. In the test models of the invention, the lower IS(%) was, the stronger the antiischemic effect of a test compound. The results were shown in Table 4.

$$IS(\%) = (\text{Sum of infract size of each slice})/(\text{Total weight of left ventricle or AAR}) \times 100 \quad \text{[Mathematical Formula 2]}$$

TABLE 4

Antiischemic activity (in vivo test using rats)

| Compound | Myocardial infarction rate (IS/AAR[1], %) | | | |
|---|---|---|---|---|
| | 0.1 mg/Kg | 0.3 mg/kg | 1.0 mg/kg | 3.0 mg/kg |
| Negative Control | | | 58.6 | |
| Cariporice | 40.5 | 37.9 | 35.4 | 27.4 |
| Example 1 | | 51.2 | | |
| Example 2 | 41.2 | 37.6 | 31.8 | 25.7 |
| Example 4 | | | 49.6 | |
| Example 5 | | | 36.6 | |
| Example 6 | 52.7 | 44.9 | 40.4 | |
| Example 8 | | | 45.9 | |
| Example 9 | | | 40.3 | |
| Example 11 | | 45.7 | | |
| Example 14 | | 54.2 | 33.3 | |
| Example 17 | | 49.9 | | |
| Example 23 | | | 37.7 | |
| Example 24 | | | 41.2 | |
| Example 25 | | | 43.0 | |
| Example 28 | 53.4 | 42.3 | 33.0 | 29.5 |
| Example 30 | | | 39.3 | |
| Example 34 | 43.3 | | 34.7 | |
| Example 35 | 42.7 | | 36.2 | |
| Example 36 | 52.4 | | 34.7 | |
| Example 37 | | | 40.2 | |
| Example 38 | 48.7 | | 27.5 | |
| Example 39 | 35.4 | 32.9 | 27.2 | |
| Example 42 | 28.4 | | | |
| Example 48 | 50.1 | | | |
| Example 49 | 43.5 | 41.5 | | |

[1]IS/AAR (infacrt size/area at risk)

As shown in the Table 4, in ischemic myocardial injury models prepared from white rats, myocardial infration size was significantly decreased by compounds of the present invention. Particularly, myocardial infration size to AAR (IS/AAR, %) was 58.6% in a vehicle-administered group, suggesting that myocardial injury by ischemia was very serious. And myocardial infration rates in a control group treated with cariporide at different concentrations of 0.1, 0.3, 1.0 and 3.0 mg/Kg were 40.5, 37.9, 35.4 and 27.4% respectively, indicating that damage by ischemia was significantly reduced dose-dependently. The compounds of Example 2, 5, 14, 23, 28, 30, 34, 35, 36, 38 and 39 showed under 40% myocardial infration rate by the administration of 0.1 mg/kg, which were similar or greater cardioprotective effect than that of cariporide (35.4%). In particular, the compound of Example 42 showed 28.4% infarction rate by the administration of 0.1 mg/kg, which was very excellent ischemic cardioprotective effect, and the compound of Example 49 also showed very significant ischemic cardioprotective effect by the administration of 0.1 and 0.3 mg/kg. The compounds of Example 6, 9, 24 and 25 showed 40.4, 40.3, 41.2 and 43.0% myocardial infarction rate by the administration of 1.0 mg/kg, indicating significant reduction of infarction rate comparing to that of negative control. The compound of Example 6 showing better improvement of cardiac function than cariporide in the isolated ischemic heart model of Experimental Example 3, represented rather reduced myocardial infarction than cariporide in an in vivo model but it was still significant and dose-dependent. The compound of Example 2 showed highly improved cardiac fuction dose-dependently compared to cariporide in the isolated ischemic heart model of Experimental Example 3, and in the case of in vivo ischemic heart model as shown in the above table 4, it reduced myocardial infration as effective as cariporide at 0.1 mg/kg and better than cariporide at 0.3, 1.0 and 3.0 mg/kg. The compounds of Example 38 ($IC_{50}$: 0.09 μM) and 39 ($IC_{50}$: 0.06 μM), which were 10 times as potent as cariporide ($IC_{50}$: 1.0 μM) on NHE-1, showed 27.5% and 27.2% myocardial infration rate by the administration of 1.0 mg/kg, which were significantly greater effect than that (35.4%) of cariporide. Especially the compound of Example 39 reduced myocardial infration to 35.4 and 32.9% even at low dose of 0.1 and 0.3 mg/kg, suggesting that the size of myocardial infration resulted from ischemia was significantly reduced comparing to cariporide. The compounds of Example 2, 34, 35, 39, 42 and 49 also showed significant myocardial infration limiting effect even with the low dose of 0.1 mg/kg, compared to negative control. In conclusion, the compounds of the present invention reduced myocardial infration rate in an in vivo ischemic heart model, indicating that they have excellent cardioprotective effect. Thus, the compounds of the present invention can be effectively used for the prevention and the treatment of ischemic heart diseases such as myocardial infration, arrhythmia, angina pectoris, etc, and also a promising candidate for a heart protecting agent applied to reperfusion therapy or cardiac surgery including coronary artery bypass graft, percutaneous transluminal coronary angioplasty, etc.

EXPERIMENTAL EXAMPLE 5

Acute Toxicity Test in Rats Via Oral Administration

The following experiments were performed to see if the compounds of Formula 1 of the present invention have acute toxicity in rats.

6-week old SPF SD line rats were used in the tests for acute toxicity. Compounds of Example 1~47 were suspended in 0.5% methyl cellulose solution and orally administered once to 2 rats per group at the dosage of 10 mg/kg/15 Ml.

Death, clinical symptoms, and weight change in rats were observed, hematological tests and biochemical tests of blood were performed, and any abnormal signs in the gastrointestinal organs of chest and abdomen were checked with eyes during autopsy.

The results showed that the test compounds did not cause any specific clinical symptoms, weight change, or death in rats. No change was observed in hematological tests, biochemical tests of blood, and autopsy. The compounds used in this experiment were evaluated to be safe substances since they did not cause any toxic change in rats up to the level of 10 mg/kg and their estimated $LD_{50}$ values were much greater than 100 mg/kg in rats.

The compounds of the present invention can be prepared in various formulations according to the purpose of use. Followings are the examples of formulations containing the compounds of the present invention as an effective ingredient, but the formulations are not limited thereto.

MANUFACTURING EXAMPLE 1

Tablets (Direct Pressurization)

5.0 mg of active compound was passed through a cieve, to which 14.1 mg of lactose, 0.8 mg of crospovidone USNF and 0.1 mg of magnesium stearate were added. After mixing them all, the mixture was pressurized, resulting in tablets.

MANUFACTURING EXAMPLE 2

Tablets (Wet Granulation)

5.0 mg of active compound was passed through a cieve, and then mixed with 16.0 mg of lactose and 4.0 mg of starch. 0.3 mg of polysorbate 80 was dissolved in distilled water and proper amount of the solution was added to the above mixture, followed by granulation. The granules were dried and cieved, and then mixed with 2.7 mg of colloidal silicon dioxide and 2.0 mg of magnesium stearate. The granules were pressurized to prepare tablets.

MANUFACTURING EXAMPLE 3

Powders and Capsules 5.0 mg of active compound was passed through a cieve, and then mixed with 14.8 mg of lactose, 10.0 mg of polyvinyl pyrrolidone and 0.2 mg of magnesium stearate. The mixture was put in solid No. 5 gelatin capsules by using a proper appatus.

MANUFACTURING EXAMPLE 4

Injectable Solutions

Injectable solutions were prepared by mixing 100 mg of active compound, 180 mg of manitol, 26 mg of $Na_2HPO_4.12H_2O$ and 2974 mg of distilled water together.

INDUSTRIAL APPLICABILITY

As explained hereinbefore, the compounds of Formula 1 of the present invention were confirmed to have potent NHE-1 inhibitory effect, to improve recovery of cardiac function from damage caused by ischemia/reperfusion in an isolated ischemic heart model and to show excellent cardioprotective effect by reducing significantly the size of myocardial infration in an in vivo ischemic heart model. Thus, a pharmaceutical composition containing furancarbonylguanidine derivatives represented by Formula 1 of the present invention and their pharmaceutically acceptable salts as an effective ingredient can be effectively used for the prevention and the treatment of ischemic heart diseases such as myocardial infration, arrhythmia, angina pectoris, etc, and also a promising candidate for a heart protecting agent applied to reperfusion therapy including thrombolytics or cardiac surgery including coronary artery bypass graft, percutaneous transluminal coronary angioplasty, etc.

The invention claimed is:

1. A furancarbonylguanidine derivative of Formula 1 or pharmaceutically acceptable salts thereof

[Formula 1]

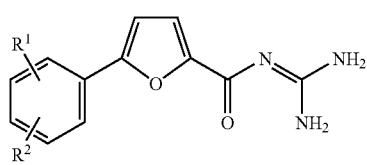

wherein

R[1] and R[2] are each independently H, F, Cl, Br, I, $CF_3$, $SO_2CH_3$, $NO_2$, $NH_2$, $C_1$~$C_5$ straight or branched alkyl, or $OR^a$; and $R^a$ is H, $CF_3$, $C_1$~$C_5$ straight or branched alkyl, or phenyl.

2. The furancarbonylguanidine derivative or pharmaceutically acceptable salts thereof as set forth in claim 1, wherein the compound of Formula 1 comprises:
 1) [5-(2-fluorophenyl)furan-2-ylcarbonyl]guanidine,
 2) [5-(3-fluorophenyl)furan-2-ylcarbonyl]guanidine,
 3) [5-(4-fluorophenyl)furan-2-ylcarbonyl]guanidine,
 4) [5-phenylfuran-2-ylcarbonyl]guanidine,
 5) [5-(2-chlorophenyl)furan-2-ylcarbonyl]guanidine,
 6) [5-(3-chlorophenyl)furan-2-ylcarbonyl]guanidine,
 7) [5-(4-chlorophenyl)furan-2-ylcarbonyl]guanidine,
 8) [5-(2-methylphenyl)furan-2-ylcarbonyl]guanidine,
 9) [5-(3-methylphenyl)furan-2-ylcarbonyl]guanidine,
 10) [5-(4-methylphenyl)furan-2-ylcarbonyl]guanidine,
 11) [5-[2-(trifluoromethyl)phenyl]furan-2-ylcarbonyl]guanidine,
 12) [5-[3-(trifluoromethyl)phenyl]furan-2-ylcarbonyl]guanidine,
 13) [5-[4-(trifluoromethyl)phenyl]furan-2-ylcarbonyl]guanidine,
 14) [5-(2-methoxyphenyl)furan-2-ylcarbonyl]guanidine,
 15) [5-(3-methoxyphenyl)furan-2-ylcarbonyl]guanidine,
 16) [5-(4-methoxyphenyl)furan-2-ylcarbonyl]guanidine,
 17) [5-(2-nitrophenyl)furan-2-ylcarbonyl]guanidine,
 18) [5-(3-nitrophenyl)furan-2-ylcarbonyl]guanidine,
 19) [5-(4-nitrophenyl)furan-2-ylcarbonyl]guanidine,
 20) [5-(2-aminophenyl)furan-2-ylcarbonyl]guanidine,
 21) [5-(3-aminophenyl)furan-2-ylcarbonyl]guanidine,
 22) [5-(4-aminophenyl)furan-2-ylcarbonyl]guanidine,
 23) [5-(2-ethylphenyl)furan-2-ylcarbonyl]guanidine,
 24) [5-(2-ethoxyphenyl)furan-2-ylcarbonyl]guanidine,
 25) [5-(2-isoproxyphenyl)furan-2-ylcarbonyl]guanidine,
 26) [5-(2-phenoxyphenyl)furan-2-ylcarbonyl]guanidine,
 27) [5-(2,6-dfluorophenyl)furan-2-ylcarbonyl]guanidine,
 28) [5-(3,5-dfluorophenyl)furan-2-ylcarbonyl]guanidine,
 29) [5-(2,4-dfluorophenyl)furan-2-ylcarbonyl]guanidine,
 30) [5-(2,4-dfluorophenyl)furan-2-ylcarbonyl]guanidine,
 31) [5-(2,3-dfluorophenyl)furan-2-ylcarbonyl]guanidine,
 32) [5-(2-chloro-6-fluorophenyl)furan-2-ylcarbonyl]guanidine,
 33) [5-(2-fluoro-5-methylphenyl)furan-2-ylcarbonyl]guanidine,
 34) [5-(2-methyl-5-fluorophenyl)furan-2-ylcarbonyl]guanidine,
 35) [5-(2-methoxy-5-fluorophenyl)furan-2-ylcarbonyl]guanidine,
 36) [5-(3,5-dichlorophenyl)furan-2-ylcarbonyl]guanidine,
 37) [5-(2,3-dichlorophenyl)furan-2-ylcarbonyl]guanidine,
 38) [5-(2,5-dichlorophenyl)furan-2-ylcarbonyl]guanidine,
 39) [5-(2-methoxy-5-chlorophenyl)furan-2-ylcarbonyl]guanidine,
 40) [5-(2-chloro-5-trifluoromethylphenyl)furan-2-ylcarbonyl]guanidine,
 41) [5-(2,6-dimethylphenyl)furan-2-ylcarbonyl]guanidine,
 42) [5-(3,5-dimethylphenyl)furan-2-ylcarbonyl]guanidine,
 43) [5-(2,5-dimethylphenyl)furan-2-ylcarbonyl]guanidine,
 44) [5-(2,3-dimethylphenyl)furan-2-ylcarbonyl]guanidine,
 45) [5-(2,6-dimethoxyphenyl)furan-2-ylcarbonyl]guanidine,
 46) [5-(2,3-dimethoxyphenyl)furan-2-ylcarbonyl]guanidine,
 47) [5-(2,5-dimethoxyphenyl)furan-2-ylcarbonyl]guanidine,
 48) [5-(2-methoxy-5-bromophenyl)furan-2-ylcarbonyl]guanidine,
 49) [5-(2-hydroxy-5-chlorophenyl)furan-2-ylcarbonyl]guanidine,
 50) [5-(2-ethoxy-5-chlorophenyl)furan-2-ylcarbonyl]guanidine, and
 51) [5-(2-isopropoxy-5-chlorophenyl)furan-2-ylcarbonyl]guanidine.

3. A method for preparing a furancarbonylguanidine compound of Formula 1, as shown in Scheme 1, comprising:
 reacting a carboxylic acid derivative compound of Formula II with guanidine in the presence of base or with an excess amount of guanidine

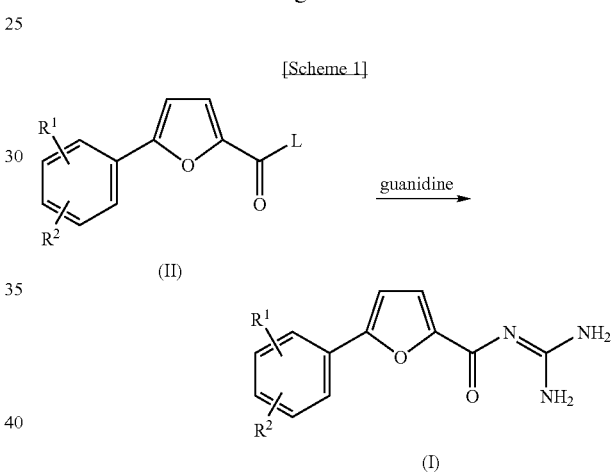

wherein

R[1] and R[2] are each independently H, F, Cl, Br, I, $CF_3$, $SO_2CH_3$, $NO_2$, $NH_2$, $C_1$~$C_5$ straight or branched alkyl, or $OR^a$;

$R^a$ is H, $CF_3$, $C_1$~$C_5$ straight or branched alkyl, or phenyl; and

L is a leaving group that is easily left by guanidine.

4. A method for preparing a furancarbonylguanidine compound of Formula 1, as shown in Scheme 2, comprising:
 reacting a carboxylic acid compound of Formula III with guanidine in the presence of a condensation agent

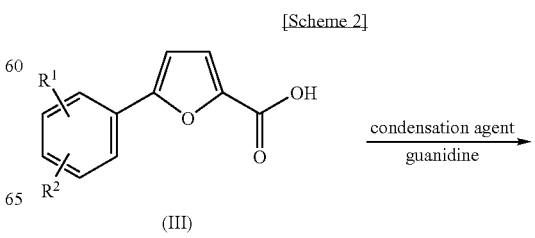

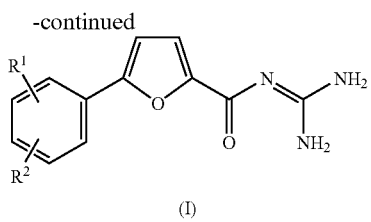

(I)

wherein $R^1$ and $R^2$ are each independently H, F, Cl, Br, I, $CF_3$, $SO_2CH_3$, $NO_2$, $NH_2$, $C_1$~$C_5$ straight or branched alkyl, or $OR^a$;

$R^a$ is H, $CF_3$, $C_1$~$C_5$ straight or branched alkyl, or phenyl.

5. The method as set forth in claim 4, wherein the condensation agent is selected from the group consisting of N, N-carbonyldiimidazole, dicyclohexylcarbodiimide (DCC), diisopropylcarbodiimide (DIPC), 1-ethyl-3-(3-dimethylaminopropyl) carbodiimide (WSC) and diphenylphosphonylazide (DPPA).

6. A method for preparing a furan compound having a benzene ring at the $5^{th}$ site, as shown in Scheme 3a, comprising:

reacting a phenylboronic acid or stanylphenyl derivative compound of Formula IV with a 5-halofuran compound of Formula V in the presence of a palladium catalyst, which is a Stille-type coupling or Suzuki-type coupling, to form a compound of Formula $II_1$

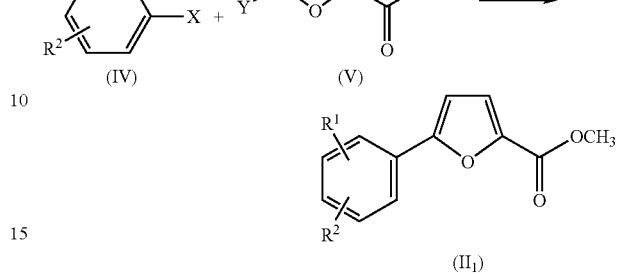

wherein $R^1$ and $R^2$ are each independently H, F, Cl, Br, I, $CF_3$, $SO_2CH_3$, $NO_2$, $NH_2$, $C_1$~$C_5$ straight or branched alkyl, or $OR^a$;

$R^a$ is H, $CF_3$, $C_1$~$C_5$ straight or branched alkyl, or phenyl;

X is $B(OH)_2$, $BCl_2$, $BBr_2$, $SnBu_3$, $SnMe_3$, or $ZnCl$, and

Y is a halogen or $OSO_2CF_3$ wherein the halogen is Br, I or Cl.

7. A composition containing furancarbonylguanidine derivative or pharmaceutically acceptable salts thereof of claim 1.

* * * * *